US009434681B2

(12) United States Patent
Uhrich et al.

(10) Patent No.: US 9,434,681 B2
(45) Date of Patent: Sep. 6, 2016

(54) MACROMOLECULES FOR TREATING ATHEROSCLEROSIS

(71) Applicant: RUTGERS, THE STATE UNIVERSITY OF NEW JERSEY, New Brunswick, NJ (US)

(72) Inventors: Kathryn E. Uhrich, New Brunswick, NJ (US); Dawanne E. Poree, New Brunswick, NJ (US); Prabhas Moghe, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/407,403

(22) PCT Filed: Jun. 17, 2013

(86) PCT No.: PCT/US2013/046177
§ 371 (c)(1),
(2) Date: Dec. 11, 2014

(87) PCT Pub. No.: WO2013/188882
PCT Pub. Date: Dec. 19, 2013

(65) Prior Publication Data
US 2015/0175528 A1 Jun. 25, 2015

Related U.S. Application Data

(60) Provisional application No. 61/660,156, filed on Jun. 15, 2012.

(51) Int. Cl.
*C07C 235/10* (2006.01)
*C07C 69/708* (2006.01)

(52) U.S. Cl.
CPC .......... *C07C 235/10* (2013.01); *C07C 69/708* (2013.01)

(58) Field of Classification Search
None
See application file for complete search history.

(56) References Cited

U.S. PATENT DOCUMENTS

| 4,065,598 | A | 12/1977 | Takahashi et al. |
| 4,938,949 | A | 7/1990 | Borch et al. |
| 6,328,988 | B1 | 12/2001 | Uhrich et al. |
| 6,365,146 | B1 | 4/2002 | Uhrich et al. |
| 6,497,895 | B2 | 12/2002 | Uhrich et al. |

(Continued)

FOREIGN PATENT DOCUMENTS

| JP | 06-145341 | 5/1994 |
| WO | 0065024 A2 | 11/2000 |

(Continued)

OTHER PUBLICATIONS

Plourde et al., Biomacromolecules 2009, 10, 1381-1391.*

(Continued)

*Primary Examiner* — Karl J Puttlitz
(74) *Attorney, Agent, or Firm* — Viksnins Harris & Padys PLLP

(57) ABSTRACT

The invention includes compounds of the formula I and formula II and salts thereof, as well as methods for using the compounds of formula I and formula II for treating atherosclerosis. The invention also includes compounds of formula III and (2l) and salts thereof, as well as methods of using the compounds of formula III and (2l) for treating atherosclerosis. The invention also includes methods of encapsulating molecules using the compounds of the invention.

20 Claims, 3 Drawing Sheets

A.

B.

(56) References Cited

U.S. PATENT DOCUMENTS

| | | | |
|---|---|---|---|
| 7,262,221 | B2 | 8/2007 | Uhrich et al. |
| 7,470,802 | B2 | 12/2008 | Uhrich et al. |
| 8,192,754 | B2 | 6/2012 | Uhrich et al. |
| 8,846,850 | B2 | 9/2014 | Uhrich et al. |
| 2004/0198641 | A1 | 10/2004 | Uhrich et al. |
| 2005/0089504 | A1 | 4/2005 | Uhrich et al. |
| 2008/0057026 | A1 | 3/2008 | Uhrich et al. |
| 2009/0175932 | A1 | 7/2009 | Uhrich et al. |
| 2011/0008396 | A1 | 1/2011 | Moghe et al. |
| 2011/0229416 | A1 | 9/2011 | Uhrich et al. |
| 2012/0022159 | A1 | 1/2012 | Uhrich et al. |
| 2012/0039983 | A1 | 2/2012 | Uhrich et al. |
| 2012/0219598 | A1 | 8/2012 | Uhrich et al. |
| 2012/0225926 | A1 | 9/2012 | Uhrich et al. |
| 2014/0120057 | A1 | 5/2014 | Uhrich et al. |

FOREIGN PATENT DOCUMENTS

| | | | |
|---|---|---|---|
| WO | 0105873 | A1 | 1/2001 |
| WO | 03005959 | A2 | 1/2003 |
| WO | 03047518 | A2 | 6/2003 |
| WO | 03103594 | A2 | 12/2003 |
| WO | 2009039505 | * | 3/2009 |
| WO | 2009039505 | A1 | 3/2009 |

OTHER PUBLICATIONS

Database Caplus Chemical Abstracts Service, Columbus, Ohio, US; Database Accession No. 2009:524636, Abstract of Plourde et al., Biomacromolecules (2009), 10(6), 1381-1391.*

Tian et al., Macromolecules 2004, 37, 538-543.*

Database Caplus Chemical Abstracts Service, Columbus, Ohio, US; Database Accession No. 138:321682, Abstract of Tian et al., Polymer Preprints (American Chemical Society, Division of Polymer Chemistry) (2002), 43(2), 719-720.*

Poree et al., Biomacromolecules (2013), 14(8), 2463-2469.*

U.S. Appl. No. 14/847,986.

Allen, et al., "Nano-engineering block copolymer aggregates for drug delivery", Colloids and Surfaces B: Biointerfaces 16:3-27.

Astafieva, et al., "Critical micellization phenomena in block polyelectrolyte solutions", Macromolecules 26 (26), 7339-7352 (1993).

Boullier, et al., "Phosphocholine as a pattern recognition ligand for CD36", Journal of Lipid Research, vol. 46, 969-976 (2005).

Brown, et al., "Lipoprotein metabolism in the macrophage: implications for cholesterol deposition in atherosclerosis", Annu Rev Biochem 52, 223-261 (1983).

Broz, et al., "Cell targeting by a generic receptor-targeted polymer nanocontainer platform", J Control Release 102 (2), 475-488 (2005).

Camejo, et al., "The extracellular matrix on atherogenesis and diabetes-associated vascular disease", Atherosclerosis Supplements, vol. 3, pp. 3-9, 2002.

Gammas, et al., "Functional poly[(ethylene oxide)-co-(beta-benzyl-L-aspartate)] polymeric micelles: block aopolymer synthesis and micelles formation", Macromol. Chem. Phys., 196, pp. 1899-1905, 1995.

Chemical Abstract of, JP-6305820, 1994.

Chnari, et al., "Engineered polymeric nanoparticles for receptor-targeted blockage of oxidized low density lipoprotein uptake and atherogenesis in macrophages", Biomacromolecules 7(6), 1796-1805 (2006).

Chnari, et al., "Nanoscale anionic macromolecules can inhibit cellular uptake of differentially oxidized LDL", Biomacromolecules 7 (2), 597-603 (2006).

Chnari, et al., "Nanoscale anionic macromolecules for selective retention of low-density lipoproteins", Biomaterials 26 (17), 3749-3758 (2005).

De Winther, et al., "Macrophage scavenger receptor class A: A multifunctional receptor in atherosclerosis", Arterioscler Thromb Vase Biol., 20(2), 290-297 (2000).

Djodjevic, et al., "Polymeric Micelles Based on Amphiphilic Scorpion-like Macromolecules: Novel Carriers for Water-Insoluble Drugs", Pharmaceutical Research, 22(1), pp. 24-32, 2005.

Djordjevic, et al., "Amphiphilic Scorpion-like Macromolecules as Micellar Nanocarriers", Journal of Bioactive and Compatible Polymers, vol. 23 (6), 532-551 (2008).

Djordjevic, et al., "Amphiphilic Star-Like Macromolecules as Novel Carriers for Topical Delivery of Nonsteroidal Anti-Inflammatory Drugs", AAPS PharmSci, 5 (4), pp. 1-12, 2003.

Gao, et al., "A model of micellization for block copolymers in solutions", Macromolecules, vol. 26, pp. 7353-7360, 1993.

Gao, et al., "Binding of proteins to copolymers of varying hydrophobicity", Biopolymers 49 (2), 185-193 (1999).

Gitsov, et al., "Micelles with highly branched nanoporous interior: solution properties and binding capabilities of amphiphilic copolymers with linear dendritic architecture", Journal of Polymer Science: Part A: Polymer Chemistry, vol. 38, pp. 2711-2727, 2000.

Goldstein, et al., "Binding site on macrophages that mediates uptake and degradation of acetylated low density lipoprotein, producing massive cholesterol deposition", Proc Natl Acad Sci 76 (1), 333-337 (1979).

Guaderrama-Diaz, et al., "Control of scavenger receptor-mediated endocytosis by novel ligands of different length", Mol Cell Biochem 271 (1-2), 123-132 (2005).

Harmon, et al., "In Vitro Evaluation of Amphiphilic Macromolecular Nanocarriers for Systemic Drug Delivery", Journal of Bioactive and Compatible Polymers, 24, pp. 185-197, 2009.

Hehir, et al, "Carbohydrate composition of amphiphilic macromolecules influences physicochemical properties and bnding to atherogenic scavenger receptor A", Acta Biomater 8 (11), 3956-3962 (2012).

Ihre, et al., "Fast and Convenient Divergent Synthesis of Aliphatic Ester Dendrimers by Anhydride Coupling", J. Am. Chem, Soc. 123 (25), 5908-5917 (2001).

Iverson, et al., "Controllable inhibition of cellular uptake of oxidized low-density lipoprotein: Structure-function relationships for nanoscale amphiphilic polymers", Acta Biomaterialia 6, 3081-3091 (2010).

Iverson, et al., "Dual use of amphiphilic macromolecules as cholesterol efflux triggers and inhibitors of macrophage athero-inflammation", Biomaterials 32, 8319-8327 (2011).

Kalyanasundaram, et al., "Environmental effects on vibronic band intensities in pyrene monomer fluorescence and their application in studies of micellar systems", J. Am. Chem. Soc. 99 (7), 2039-2044 (1977).

Kataoka, et al., "Block copolymer micelles for drug delivery: design, characterization and biological significance", Adv Drug Deily Rev. 47(1):113-31.

Kreig, et al., "Micelle formation of randomly grafted copolymers in slightly selective solvents", Journal of Chemical Physics, vol. 115, No. 13, pp. 6243-6251, 200t.

Langer, et al., "New methods of drug delivery", Science, 249, pp. 1527-1533, 1990.

Li, et al. "The macrophage foam cell as a target for therapeutic intervention", Nature Medicine 8 (11), 1235-1242 (2002).

Liu, et al. "Unimolecular micelles: Synthesis and characterization of amphiphilic polymer systems", Journal of Polymer Science, Part A:P Polymer Chemistry, 37(6), 703-711 (1999).

Makino, et al., "Control of in vivo blood clearance time of polymeric micelle by stereochemistry of amphiphilic polydepsipeptides", J. Control Release 161 (3), 821-825 (2012).

Meng, et al., "Mesomorphic behavior and optical properties of liquid-crystalline polysiloxanes bearing different chiral groups", Journal of Applied Polymer Science, vol. 114 (4), 2195-2203 (2009).

Moghimi, et al., "Exploiting bone marrow microvascular structure for drug delivery and future therapies", Advanced Drug Delivery Reviews, vol. 17, pp. 61-73, 1995.

Moghimi, et al., "Long-circulating and target-specific nanoparticles: theory to practice", J. Pharm. Rev. vol. 53(2), pp. 283-318, 2001.

Moore, et al., "Room temperature polyesterification", Macromolecules 23 (1), 65-70 (1990).

(56) References Cited

OTHER PUBLICATIONS

Otsuka, et al., "Self-assembly of poly(ethylene glycol)-based block copolymers for biomedical applications", Current Opinion in Colloid & Interface Science 6(1):3-10.

Papisov, et al., "Modeling in vivo transfer of long-circulating polymers (two classes of long circulating polymers and factors affecting their transfer in vivo)", Advanced Drug Delivery Reviews, vol. 16, pp. 127-139, 1995.

Patent Cooperation Treaty, International Search Authority, Search Report and Written Opinion for PCT/JS2013/046177, 12 pages, Oct. 1, 2013.

Petit, et al., "Interactions of hydrophobically modified poly(sodium acrylate) with globular proteins", Colloid Polym Sci 273, 777-781 (1995).

Podrez, et al., "Macrophage scavenger receptor CD36 is the major receptor for LDL modified by monocyte-generated reactive nitrogen species", J. Clin Invest 105 (8), 1095-1108 (2000).

Porcar, et al., "Association between Protein Particles and Long Amphiphilic Polymers: Effect of the Polymer Hydrophobicity on Binding Isotherms", Macromolecules 32 (12), 3922-3929 (1999).

Poree, et al., "Nanoscale Amphiphilic Macromolecules with Variable Lipophilicity and Stereochemistry Modulate Inhibition of Oxidized Low-Density Lipoprotein Uptake", Biomacromolecules 14 (8), 3463-2469 (2013).

Reeve, et al., "Polylactide stereochemistry: effect on enzymatic degradability", Macromolecules 27 (3), 825-831 (1994).

Rousselle, et al., "New advances in the transport of doxorubicin through the blood-brain barrier by a peptide vector-mediated strategy", Molecular Pharmacology, Vo. 57, pp. 679-686, 2000.

Schmalenberg, et al., "Cytotoxicity of a unimolecular polymeric micelle and its degradation products", Biomacromolecules 2, pp. 851-855, 2001.

Sparks, et al., "Efficient intracellular siRNA delivery by ethyleneimine-moditied amphiphilic macromolecules", Macromol Biosci 11 (9), 1192-1200 (2011).

Steinberg, et al., "Low density lipoprotein oxidation and its pathobiological significance", Journal of Biological chemistry vol. 272 (34), 20963-20966 (1997).

Sun, et al., "Functional biointerface materials inspired from nature", Chem Soc Rev 40 (5), 2909-2921 (2011).

Sun, et al., "Stereospecific interaction between immune cells and chiral surfaces", J. Am. Chem. Soc. 129 (6), 1496-1497 (2007).

Tao, et al., "Novel amphiphilic macromolecules and their in vitro characterization as stabilized micellar drug delivery systems", J. Colloid Interface Sci 298 (1), 102-110 (2006).

Temsamani, et al., "Brain drug delivery technologies: novel approaches for transporting therapeutics", PSTT, vol. 3, No. 5, pp. 155-162, 2000.

Tian, et al., "Design and synthesis of amphiphilic poly(ethylene glycol) derivaties as a micellar drug delivery system", Polymer Preprints, 43(2), 719-720 (2002).

Tian, et al., "Design and synthesis of amphiphilic poly(ethylene glycol) derivatives as a micellar drug delivery system", Abstracts of Papers, Part 2, 224, (1-2), abstract 748, 224th ACS National Meeting (2002).

Tian et al., "Novel amphiphilic macromolecules for drug delivery applications: design, synthesis and characterization", in Dissertation, New Brunswick, New Jersey, pp. 13-48, 114-138 and 160-175, 2004.

Torchilin, et al., "Structure and design of polymeric surfactant-based drug delivery systems", J Control Release 73 (2-3):137-72.

Tuzar, et al., "Micelles of Block and Graft Copolymers in Solutions", Surface and Colloid Science, vol. 15, pp. 1-83, 1993.

Wang, et al., "Chiral Design for Polymeric Biointerface: The Influence of Surface Chirality on Protein Adsorption", Advanced Functional Materials, vol. 21 (17), 3276-3281 (2011).

Wang, et al., "Comparison of PEG chain length and density on amphiphilic macromolecular nanocarriers: Self-assembled and unimolecular micelles", Acta Biomaterialia, 5, pp. 883-892, 2009.

Wang, et al., "Nanoscale amphiphilic macromolecules as lipoprotein inhibitors: the role of charge and architecture", Int. J. Nanomedicine, 2(4), pp. 697-705, 2007.

Wang, et al., "Stereochemistry triggered differential cell behaviours on chiral polymer surfaces", Soft Matter 6, 3851-3855 (2010).

Williams, et al., "The response-to-retention hypothesis of early atherogenesis", Arteriosclerosis, Thrombosis & Vascular Biology, vol. 15, No. 5, pp. 551-561, 1995.

York, et al., "Kinetically assembled nanoparticles of bioactive macromolecules exhibit enhanced stability and cell-targeted biological efficacy", Adv Mater 24 (6), 733-739 (2012).

Yoshiizumi, et al., "2,4-Bis(octadecanoylamino)benzenesulfonic acid sodium salt as a novel scavenger receptor Inhibitor with low molecular weight", Bioorg Med Chem Lett, 14 (11), 2791-2795 (2004).

Yoshimoto, et al., "Growth stimulation and epidermal growth factor receptor induction in cyclooxygenase-overexpressing human colon carcinoma cells", Adv Exp Med Biol, 403-407 (2002).

Zeng, et al., "A polymeric micelle system with a hydrolysable segment for drug delivery", J. Biomater Sci Polym Ed. 17 (5), 591-604 (2006).

Zhang, et al., "Chiral biointerface materials", Chem Soc Rev 41 (5), 1972-1984 (2012).

Zhu, et al", "Super Microcapsules" (SMC. I. Preparation and Characterization of Star Polyethylene Oxide (POE)-Polylactide (PLA) Copolymers", J. Polym. Sci. Polm. Chem., vol. 27, p. 2151, 1989.

\* cited by examiner

A.

B.

A.

B.

\# P<0.05 – compared to no polymer condition
\* P<0.05 – compared to 2l

MACROMOLECULES FOR TREATING ATHEROSCLEROSIS

CROSS-REFERENCE TO RELATED APPLICATION(S)

This application claims priority from U.S. Provisional Application No. 61/660,156, filed Jun. 15, 2012, which application is herein incorporated by reference.

STATEMENT OF GOVERNMENT RIGHTS

The invention was made with government support under R21 HL093753 and R01 HL107913-01 awarded by the National Institutes of Health. The government has certain rights in the invention.

BACKGROUND OF THE INVENTION

Atherosclerosis, a disease characterized by occlusion of the arteries, is triggered by the build-up of oxidized low density lipoprotein (oxLDL) in vascular intima (Li, et al., The macrophage foam cell as a target for therapeutic intervention. *Nat Med* 2002, 8 (11), 1235-1242). The oxLDL accumulation generates an inflammatory response, resulting in the recruitment of circulating monocytes, followed by their differentiation into macrophages, resulting in the upregulation of macrophage scavenger receptors (Yoshimoto, et al., Growth stimulation and epidermal growth factor receptor induction in cyclooxygenase-overexpressing human colon carcinoma cells. *Adv Exp Med Biol* 2002, 507, 403-7). The uptake of oxLDL is mediated by these scavenger receptors, namely scavenger receptor A (SR-A) and cluster of differentiation 36 (CD36) (Goldstein, J. L.; et al., Binding site on macrophages that mediates uptake and degradation of acetylated low density lipoprotein, producing massive cholesterol deposition. *Proc Natl Acad Sci USA* 1979, 76 (1), 333-7; Podrez, E. A.; et al., Macrophage scavenger receptor CD36 is the major receptor for LDL modified by monocyte-generated reactive nitrogen species. *J Clin Invest* 2000, 105 (8), 1095-108; de Winther, M. P.; et al., Macrophage scavenger receptor class A: A multifunctional receptor in atherosclerosis. *Arteriosclerosis, thrombosis, and vascular biology* 2000, 20 (2), 290-7), leading to unregulated cholesterol accumulation and foam cell formation, a key characteristic of the onset of atherogenesis (Brown, M. S.; Goldstein, J. L., Lipoprotein metabolism in the macrophage: implications for cholesterol deposition in atherosclerosis. *Annual review of biochemistry* 1983, 52, 223-61; Steinberg, D., Low density lipoprotein oxidation and its pathobiological significance. *J Biol Chem* 1997, 272 (34), 20963-6).

To date, cholesterol-lowering therapies (i.e., statins) are the most common methods for management of the long-term effects of atherosclerosis. These drugs indirectly ameliorate the cascade of atherosclerosis by decreasing cholesterol synthesis; however, the ultimate impact on the deposition of oxLDL in the blood vessel walls has not been clearly established. A more direct and promising approach in the treatment and prevention of atherosclerosis involves designing functional inhibitors against scavenger receptors to abrogate uncontrolled oxLDL uptake (Boullier, A.; et al., Phosphocholine as a pattern recognition ligand for CD36. *J Lipid Res* 2005, 46 (5), 969-976; Yoshiizumi, K.; et al., 2,4-Bis(octadecanoylamino)benzenesulfonic acid sodium salt as a novel scavenger receptor inhibitor with low molecular weight. *Bioorg Med Chem Lett* 2004, 14 (11), 2791-2795; Guaderrama-Diaz, M.; et al., Control of scavenger receptor-mediated endocytosis by novel ligands of different length. *Mol Cell Biochem* 2005, 271 (1-2), 123-132; Broz, P.; et al., Cell targeting by a generic receptor-targeted polymer nano-container platform. *J Control Release* 2005, 102 (2), 475-488).

Nanoscale amphiphilic macromolecules (AMs) capable of inhibiting oxLDL uptake through competitive inhibition of SRA and CD36 scavenger receptors in IC21 macrophage cells have been reported (Chnari, E.; et al., *Biomacromolecules* 2006, 7, 1796-1805). Comprised of a mucic acid backbone, four aliphatic chains, and a poly(ethylene glycol) (PEG) tail, these biocompatible AMs form nanoscale micelles in aqueous media at relatively low critical micelle concentrations ($10^{-7}$ M). There remains a need for therapeutic agents that treat athereosclerosis and agents that do so through alternative mechanisms of action.

SUMMARY OF THE INVENTION

The inventors have discovered that amphiphilic molecules (e.g. AMs) of formula I and formula II are useful in inhibiting the uptake of LDL and thus may be useful for treating athereosclerosis.

Accordingly, the invention provides a compound of formula I or formula II:

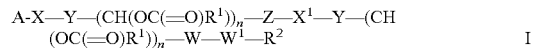

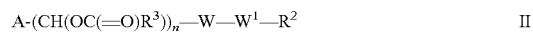

wherein;

A is an anionic group;
X is a $(C_1$-$C_4)$alkylene;
Y is —NHC(=O)—;
each n is independently 2, 3, 4, 5 or 6;
Z is —C(=O)NH—;
$X^1$ is a $(C_2$-$C_6)$alkylene;
W is —C(=O)—, —C(=S)—, or is absent;
$W^1$ is O, S or NH;
each $R^1$ is independently a hydrophobic chain;
$R^2$ is a polyether; and
each $R^3$ is independently $(C_1$-$C_8)$alkyl wherein each $(C_1$-$C_8)$alkyl is independently substituted with one or more (e.g. 1, 2, 3 or 4) —O(C=O)$R^1$ groups;
or a salt thereof.

The invention also provides a pharmaceutical composition comprising a compound of formula I or formula II or a pharmaceutically acceptable salt thereof, and a pharmaceutically acceptable carrier.

The invention also provides a method for reducing LDL in a mammal (e.g., a human) comprising administering an effective amount of a compound of formula I or formula II as described herein, or a pharmaceutically acceptable salt thereof, to the mammal.

The invention also provides a method for preventing the uptake of LDL by a cell comprising contacting the cell with a compound of formula I or formula II or a pharmaceutically acceptable salt thereof as described in herein.

The invention also provides a method for inhibiting atherosclerosis or atherosclerotic development in a mammal (e.g., a human), comprising administering an anti-atherosclerosis or anti-atherosclerotic development amount of a compound of formula I or formula II as described herein, or a pharmaceutically acceptable salt thereof, to the mammal.

The invention also provides a compound of formula I or formula II or a pharmaceutically acceptable salt thereof for use in medical therapy.

The invention also provides a compound of formula I or formula II or a pharmaceutically acceptable salt thereof for the prophylactic or therapeutic treatment of atherosclerosis.

The invention also provides the use of a compound of formula I of formula II or a pharmaceutically acceptable salt thereof to prepare a medicament for inhibiting atherosclerosis or atherosclerotic development in a mammal (e.g., a human).

The invention also provides the use of a compound of formula I of formula II or a pharmaceutically acceptable salt thereof to prepare a medicament for reducing LDL in a mammal (e.g., a human).

The invention also provides the use of a compound of formula I of formula II or a pharmaceutically acceptable salt thereof to prepare a medicament for preventing the uptake of LDL by a cell in a mammal (e.g., a human).

The invention also provides intermediates and processes useful for preparing compounds of formula I or formula II as described herein.

The invention also provides a compound of formula (2l):

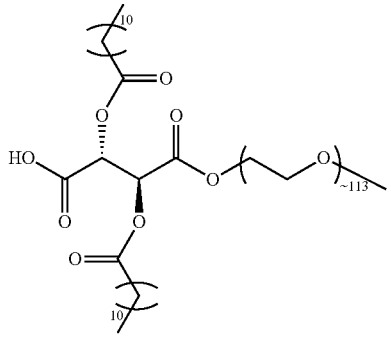

or a salt thereof.

The invention provides a compound of formula III:

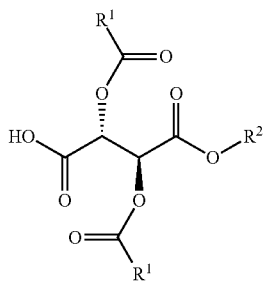

III wherein: each $R^1$ is independently a hydrophobic chain; and each $R^2$ is a polyether; or a salt thereof.

The invention also provides methods of using a compound of formula III or (2l) or salts thereof, compositions comprising a compound of formula III or (2l) or salts thereof, and intermediates and processes useful for preparing a compound of formula III or (2l) as described herein.

DETAILED DESCRIPTION

Figure 1:
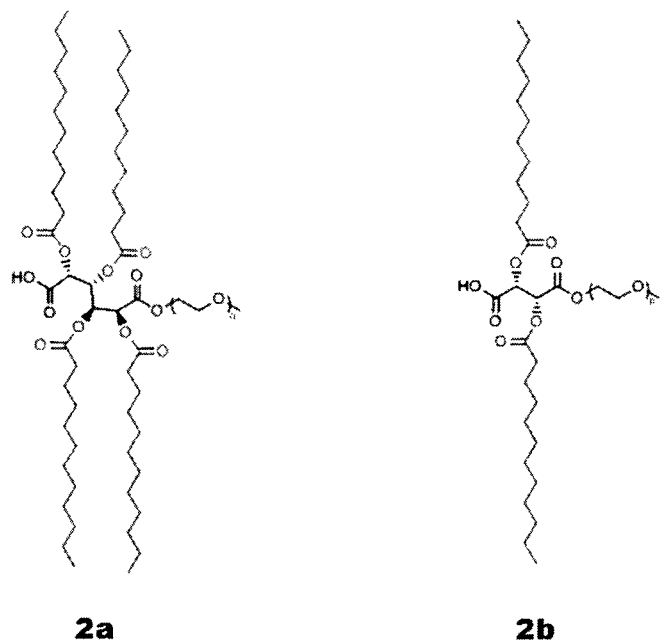
FIG. 1A depicts the structures of macromolecules (2a) and (2b) bearing 4- and 2-aliphatic arms, respectively.
FIG. 1B depicts AM (2a) and (2b) inhibition of oxLDL in PBMC macrophages.
Figure 1:
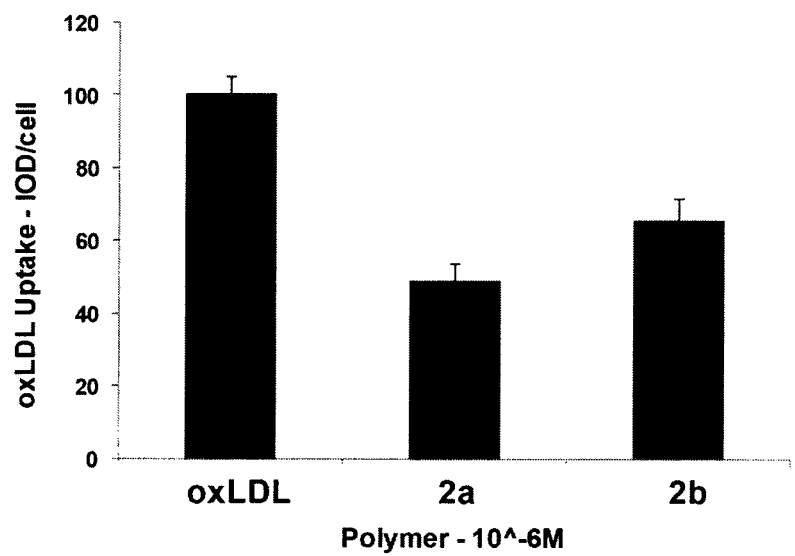

The term "amine" as used herein refers to —$NH_2$. The term "amine" also refers to —$NHR_b$ wherein each $R_b$ is ($C_1$-$C_6$)alkyl, —($C_1$-$C_6$)alkylaryl or aryl.

The term "anionic group" refers to groups that are negatively charged or groups that are capable of supporting a negative charge. Anionic groups include but are not limited to carboxy (—$CO_2H$), —$SO_3H$, —$NHSO_2R_c$, $PO_3H$ or $NO_2$ or salts thereof, wherein $R_c$ is $CF_3$, ($C_1$-$C_6$)alkyl, —($C_1$-$C_6$)alkylaryl or aryl. The salts of the anionic groups, including inorganic and organic salts, are readily known by those skilled in the art.

Halo refers to fluoro, chloro, bromo, or iodo.

Alkyl, alkylene, alkene, alkenylene, alkyne, alkynylene, alkoxy, etc. denote both straight and branched groups; but reference to an individual radical such as propyl embraces only the straight chain radical, a branched chain isomer such as isopropyl being specifically referred to.

Alkyl or alkylene refers to a straight or branched hydrocarbon group.

Alkene or alkenylene refers to a straight or branched hydrocarbon group that has one or more carbon-carbon double bonds.

Alkyne or alkynylene refers to a straight or branched hydrocarbon group that has one or more carbon-carbon triple bonds.

Alkoxy refers to the group —O-alkyl (e.g. a group wherein a alkyl radical is connected to a molecule through an oxygen atom).

Carboxy refers to —$CO_2H$.

The term "hydrophobic chain" refers to a chain comprising one or more ($C_1$-$C_{24}$)alkyl, ($C_2$-$C_{24}$)alkene, ($C_2$-$C_{24}$) alkyne or aryl groups or combinations thereof. The hydrophobic chain is generally hydrocarbon in nature and lacks polarity. The term hydrophobic chain also includes fatty acids or fatty acid residues.

As used herein, the term fatty acid or fatty acid residue includes fatty acids and fatty oils as conventionally defined, for example, long-chain aliphatic acids that are found in natural fats and oils. Fatty acids typically comprise from about 2 to about 24 carbon atoms. In one embodiment the fatty acids comprise from about 6 to about 18 carbon atoms. The term "fatty acid" encompasses compounds possessing a straight or branched aliphatic chain and an acid group, such as a carboxylate, sulfonate, phosphate, phosphonate, and the like. The "fatty acid" compounds are capable of "esterifying" or forming a similar chemical linkage with hydroxy groups of the compounds of formula I or formula II. Examples of suitable fatty acids include caprylic, capric, lauric, myristic, myristoleic, palmitic, palmitoleic, stearic, oleic, linoleic, eleostearic, arachidic, behenic, erucic, and like acids. Fatty acids can be derived from suitable naturally occurring or synthetic fatty acids or oils, can be saturated or unsaturated, and can optionally include positional or geometric isomers. Many fatty acids or oils are commercially available or can be readily prepared or isolated using procedures known to those skilled in the art.

As used herein, the term polyether includes poly(alkylene oxides) having between about 2 and about 150 repeating units. Typically, the poly(alkylene oxides) have between about 50 and about 115 repeating units. The alkylene oxide units contain from 2 to 10 carbon atoms and may be straight chained or branched. In one embodiment the alkylene oxide units contain from 2 to 10 carbon atoms. Poly(ethylene glycol) (PEG) is preferred. Alkoxy-, amino-, carboxy-, and sulfo-terminated poly(alkylene oxides) are preferred, with methoxy-terminated poly(alkylene oxides) being more preferred.

In one embodiment the polyether has the following structure:

$$R_5—(R_6—O—)_a—R_6—$$

wherein $R_5$ is a 1 to 20 carbon straight-chain or branched alkyl group, —OH, —$OR_7$, —$NH_2$, —$NHR_7$, —$NHR_7R_8$, —$CO_2H$, —$SO_3H$ (sulfo), —$CH_2$—OH, —$CH_2$—$OR_7$, —$CH_2$—O—$CH_2$—$R_7$, —$CH_2$—$NH_2$, —$CH_2$—$NHR_7$, —$CH_2$—$NR_7R_8$, —$CH_2CO_2H$, —$CH_2SO_3H$, or —O—C(=O)—$CH_2$—$CH_2$—C(=O)—O—;

$R_6$ is a 1 to 10 carbon straight-chain or branched divalent alkylene group;

each $R_7$ and $R_8$ is independently a 1 to 6 carbon straight-chain or branched alkylene group; and a is an integer from 2 to 150, inclusive.

In certain embodiments, a is an integer from 20 to 140, inclusive. In certain embodiments, a is an integer from 50 to 130, inclusive. In certain embodiments, a is an integer from 75 to 130, inclusive. In certain embodiments, a is an integer from 100 to 130, inclusive. In certain embodiments, a is 113.

In another embodiment the polyether is methoxy terminated poly(ethylene glycol).

A specific group of compounds of formula I are compounds of formula I:

$$A\text{-}X—Y—(CH(OC(=O)R^1))_n—Z—X^1—Y—(CH(OC(=O)R^1))_n—W—W^1—R^2 \quad (I)$$

wherein;
A is an anionic group;
X is a ($C_1$-$C_4$)alkylene;
Y is —NHC(=O)—;
each n is independently 2, 3, 4, 5 or 6;
Z is —C(=O)NH—;
$X^1$ is a ($C_2$-$C_6$)alkylene;
W is —C(=O)—, —C(=S)—, or is absent;
$W^1$ is O, S or NH;
each $R^1$ is independently a hydrophobic chain; and
$R^2$ is a polyether;
or a salt thereof.

Another specific group of compounds of formula I are compounds of formula Ia:

wherein;
X is a ($C_1$-$C_4$)alkylene;
n is 2, 3 4, 5 or 6;
$X^1$ is a ($C_2$-$C_6$)alkylene;
each $R^1$ is independently a hydrophobic chain; and
$R^2$ is a polyether;
or a salt thereof.

A specific group of compounds of formula II are compounds of formula II:

$$A\text{-}(CH(OC(=O)R^3))_n—W—W^1—R^2 \quad II$$

wherein;
A is an anionic group;
n is 2, 3, 4, 5 or 6;
W is —C(=O)—, —C(=S)—, or is absent;
$W^1$ is O, S or NH;
each $R^1$ is independently a hydrophobic chain;
$R^2$ is a polyether; and
each $R^3$ is independently ($C_1$-$C_8$)alkyl wherein each ($C_1$-$C_8$)alkyl is independently substituted with one or more (e.g. 1, 2, 3 or 4) —O(C=O)$R^1$ groups;
or a salt thereof.

Another specific group of compounds of formula II are compounds of formula IIa:

wherein:
n is 2, 3, 4, 5 or 6;
each $R^1$ is independently a hydrophobic chain;
$R^2$ is a polyether; and
each $R^3$ is independently ($C_1$-$C_8$)alkyl wherein each ($C_1$-$C_8$)alkyl is independently substituted with one or more (e.g. 1, 2, 3 or 4) —O(C=O)$R^1$ groups;
or a salt thereof.

Specific values listed below are values for compounds of formula I, formula II, formula Ia, formula IIa and formula III. It is to be understood that two or more values described herein may be combined.

A specific value for A is carboxy, —$SO_3H$ or —$PO_3H$.

Another specific value for A is carboxy.

A specific value for W is —C(=O)—.

A specific value for $W^1$ is O.

A specific group of compounds are compounds wherein the polyether is a poly(alkylene oxide) having between about 2 and about 150 repeating units.

A specific group of compounds are compounds wherein the alkylene oxide unit comprises straight or branched ($C_2$-$C_4$) alkylene oxide.

A specific group of compounds are compounds wherein the polyether is a poly(ethylene oxide) having between about 2 and about 150 repeating units.

A specific group of compounds are compounds wherein the polyether comprises an alkoxy-terminal group.

A specific group of compounds are compounds wherein the polyether is a methoxy-terminated poly (ethylene oxide) having between about 2 and about 150 repeating units.

A specific group of compounds are compounds wherein the polyether has the following structure:

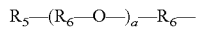

wherein $R_5$ is a 1 to 20 carbon straight-chain or branched alkyl group, —OH, —OR$_7$, —NH$_2$, —NHR$_7$, —NHR$_7$R$_8$, —CO$_2$H, —SO$_3$H (sulfo), —CH$_2$—OH, —CH$_2$—OR$_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;

$R_6$ is a 1 to 10 carbon straight-chain or branched divalent alkylene group;

each $R_7$ and $R_8$ is independently a 1 to 6 carbon straight-chain or branched alkylene group; and a is an integer from 2 to 150, inclusive.

A specific value for $R^1$ is $(C_1$-$C_{24})$alkyl, $(C_2$-$C_{24})$alkene or $(C_2$-$C_{24})$alkyne.

Another specific value for $R^1$ is independently a fatty acid, wherein the fatty acid is caprylic, capric, lauric, myristic, myristoleic, palmitic, palmitoleic, stearic, oleic, linoleic, arachidic, behenic, or erucic acid, or a mixture thereof.

Another specific value for $R^1$ is $(C_6$-$C_{18})$alkyl.

Another specific value for $R^1$ is $(C_{10}$-$C_{12})$alkyl.

Another specific value for $R^1$ is $(CH_2)_{10}CH_3$.

A specific value for n is 2 or 4.

In certain embodiments, a specific value for n is 2.

In certain embodiments, a specific value for n is 4.

A specific value for X is a methylene.

A specific value for $X^1$ is an ethylene.

A specific value for $R^3$ is $(C_1$-$C_8)$alkyl wherein each $(C_1$-$C_8)$alkyl is independently substituted with two or more —O(C=O)R$^1$ groups.

Another specific value for $R^3$ is $(C_1$-$C_8)$alkyl wherein each $(C_1$-$C_8)$alkyl is independently substituted with two —O(C=O)R$^1$ groups.

Another specific value for $R^3$ is $(C_3$-$C_6)$alkyl wherein each $(C_3$-$C_6)$alkyl is independently substituted with two —O(C=O)R$^1$ groups.

A specific group of compounds are compounds wherein the polyether has the following structure:

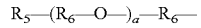

wherein $R_5$ is —OR$_7$;

$R_6$ is a 2 to 4 carbon straight-chain or branched divalent alkylene group;

$R_7$ is a 1 to 2 carbon straight-chain; and a is an integer from 2 to 150, inclusive.

Another specific group of compounds are compounds wherein the polyether has the following structure:

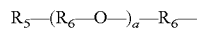

wherein $R_5$ is —OCH$_3$ or —OCH$_2$CH$_3$;

$R_6$ is ethylene (—CH$_2$CH$_2$—); and a is an integer from 2 to 150, inclusive.

Another specific group of compounds are compounds wherein the polyether has the following structure:

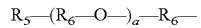

wherein $R_5$ is —OCH$_3$;

$R_6$ is ethylene (—CH$_2$CH$_2$—); and a is an integer from 2 to 150, inclusive.

In any of the above described embodiments for $R_5$—$(R_6$—O—$)_a$—$R_6$—, a can also be an integer from 20 to 140, inclusive; or an integer from 50 to 130, inclusive; or an integer from 75 to 130, inclusive; or an integer from 100 to 130, inclusive; or a is 113; or a is 112.

A specific value for X is a methylene (—CH$_2$—).

A specific value for $X^1$ is an ethylene (—CH$_2$CH$_2$—).

A specific compound of formula I or formula II includes:

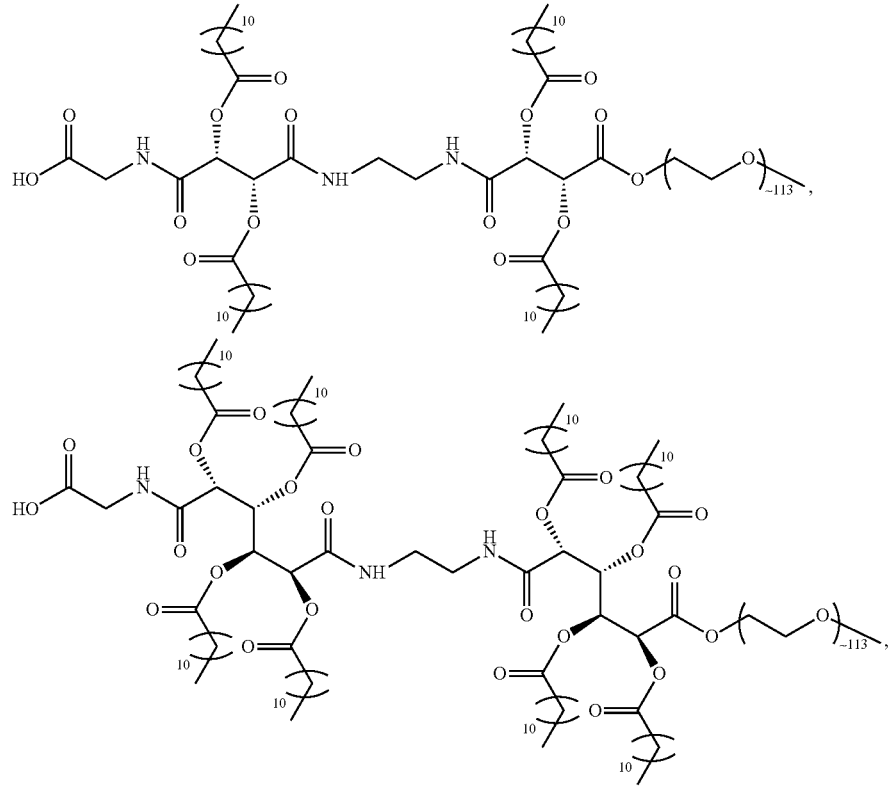

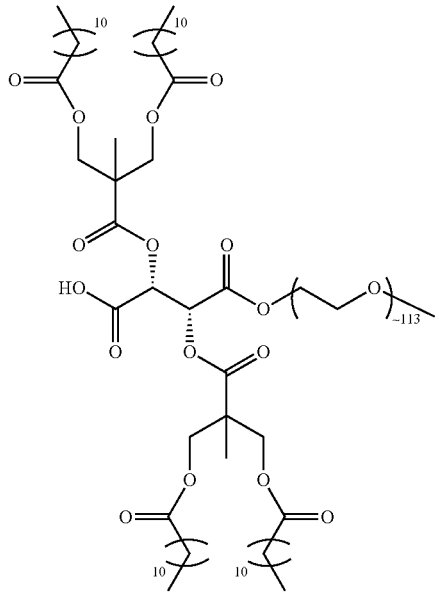
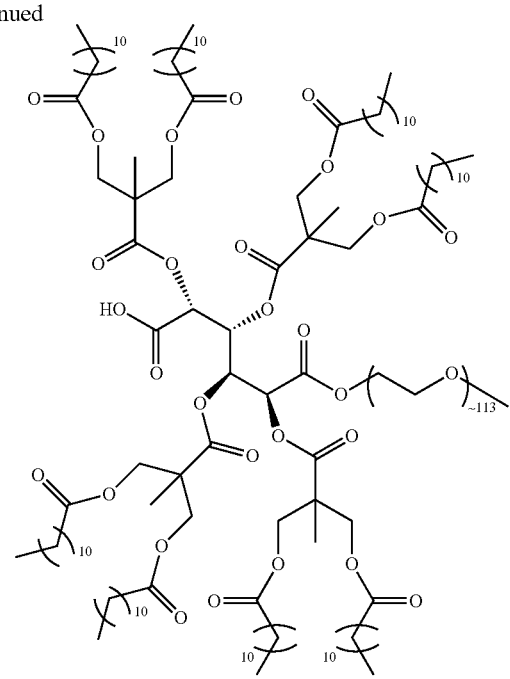
and
and salts thereof.
Another specific compound of formula I or formula II includes:
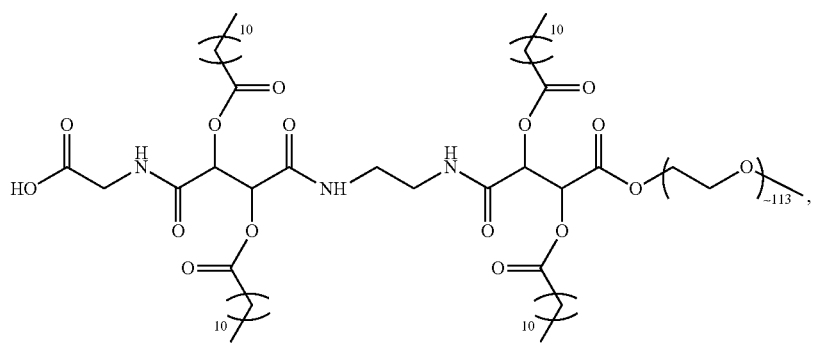
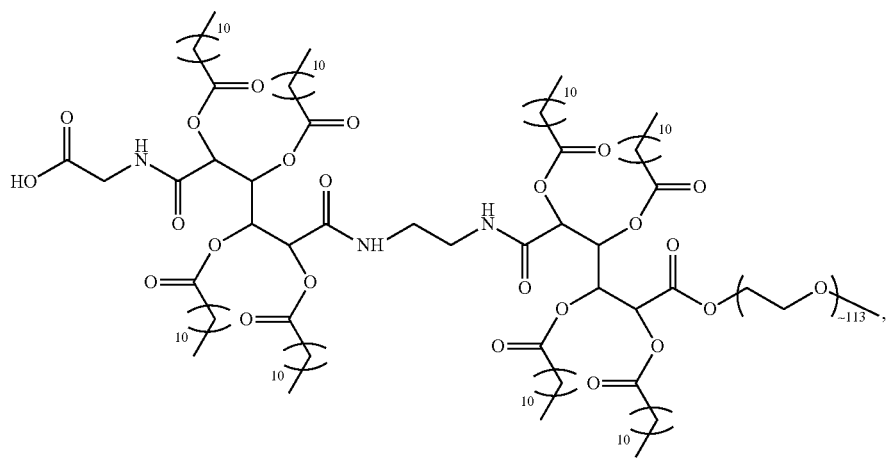

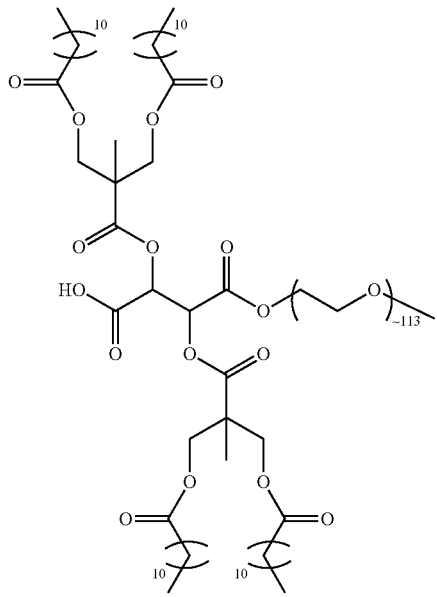

and

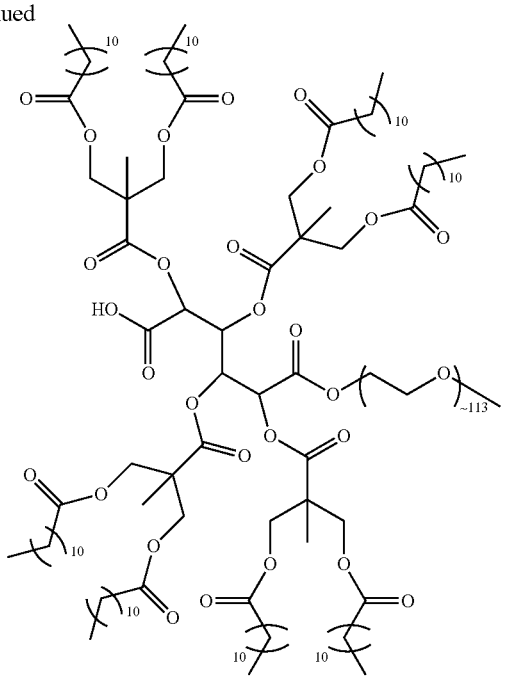

and salts thereof.

In cases where compounds are sufficiently basic or acidic, a salt of a compound of formula I or formula II can be useful as an intermediate for isolating or purifying a compound of formula I or formula II. Additionally, administration of a compound of formula I or formula II as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or formula II can be formulated as pharmaceutical compositions and administered to a mammalian host, such as a human patient in a variety of forms adapted to the chosen route of administration, i.e., orally or parenterally, by intravenous, intramuscular, topical or subcutaneous routes. Thus, the compositions of the invention may be systemically administered, in combination with a pharmaceutically acceptable vehicle such as an inert diluent.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Useful dosages of the compounds of formula I or formula II can be determined by comparing their in vitro activity, and in vivo activity in animal models. Methods for the extrapolation of effective dosages in mice, and other animals, to humans are known to the art; for example, see U.S. Pat. No. 4,938,949. Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations; such as multiple inhalations from an insufflator or by application of a plurality of drops into the eye.

Certain embodiments of the invention provide a composition comprising a plurality of compounds of formula I or formula II, as described herein, in a solvent, wherein the compounds of formula I or formula II form one or more aggregate structures.

In certain embodiments, the solvent comprises water.

In certain embodiments, the solvent is water.

As used herein, the term "aggregate" means a plurality of compounds of formula I or formula II in a solvent that have organized into an ordered structure, for example, a structure having a hydrophobic core and a surrounding hydrophilic layer, or a structure having a hydrophilic core and a surrounding hydrophobic layer.

As used herein, the term "a plurality of compounds of formula I or formula II" means more than one compound of formula I or formula II. In such a plurality, each compound of formula I or formula II can have the same structure, or the plurality can include compounds of formula I or formula II that have differing structures. In one embodiment, the term "a plurality of compounds of formula I or formula II" means more than one compound of formula I or formula II, wherein each of the compounds of formula I or formula II has the same structure.

In one embodiment the invention provides a composition comprising a plurality of compounds of formula I or formula II and one or more lipids.

As used herein, the term "encapsulate" means an aggregate, having a molecule (e.g., a therapeutic agent) surrounded or partially surrounded by a plurality of compounds of formula I or formula II. In certain embodiments, the term "encapsulate" means an aggregate, having a molecule (e.g., a therapeutic agent) surrounded or partially surrounded by a plurality of compounds of formula I or formula II and one or more lipids.

As used herein, the term "stabilized encapsulate" means an aggregate, having a molecule (e.g., a therapeutic agent) surrounded or partially surrounded by a plurality of compounds of formula I or formula II. In certain embodiments, the term "stabilized encapsulate" means an aggregate, having a molecule (e.g., a therapeutic agent) surrounded or partially surrounded by a plurality of compounds of formula I or formula II and one or more lipids.

As used herein, the phrase "low-density lipoprotein (LDL)" includes "unoxidized LDL," "weakly oxidized LDL" and "oxidized LDL." LDLs bind to proteoglycans (PGs), the major low density lipoprotein (LDL)-retentive matrix molecules within the vascular intima are proteoglycans. LDL binding to PGs modifies the LDL surface, rendering the LDL susceptible to oxidation induced by $Cu^{2+}$ and macrophages. The oxidative modification of LDL lowers its localized positive charge relative to native LDL, thus reducing the affinity of LDL for anionically charged PGs. The increase in the net negative charge on oxidized LDL also leads to the reduced recognition of oxidized LDL by the classical LDL receptor, and increased recognition by the scavenger receptors on macrophages in the intima. Thus, "unoxidized low-density lipoprotein" refers to a native LDL, e.g., an LDL that has the characteristics of an LDL that is recognized by a native LDL receptor. In contrast, an "oxidized LDL (ox-LDL)" is a modified LDL recognized by scavenger receptors. By the phrase "weakly oxidized low-density lipoprotein (LDL)" is meant a mildly or partially oxidized LDL. Both unoxidized and weakly oxidized LDL have relatively high localized positive charges, e.g., due to unmodified Lys and Arg residues on apolipoprotein B-100 (ApoB-100) (LDL have a single Apo B-100 molecule on their surface) as compared to oxidized LDL. See, for example, Chnari et al., Biomaterials, 26: 3749-3758 (2005) and Chnari et al., Biomacromolecules. 2006 February; 7(2): 597-603.

By "reduction" is meant the separation or removal (e.g., lowered concentration of a substance, such as LDL) from a physiological sample or the blood stream of a subject. For example, in one embodiment of the invention, a compound of formula I or formula II is administered to a patient and becomes associated with LDL in a manner that will provide a beneficial physiological effect. For example, it is possible that the compound of formula I or formula II may cause certain forms of the LDL to be eliminated from a subject, or prevent other forms of LDL from having physiological and/or pathological activity. In certain embodiments, the compound of formula I or formula II may attach itself to LDL and cause the LDL to be eliminated from a subject, or prevent other forms of LDL from having physiological and/or pathological activity.

For example, it is also possible that the compound of formula I or formula II can inhibit the uptake of modified forms of LDL mediated by scavenger receptors (e.g., scavenger receptor A (SR-A) or CD36) and counteract cholesterol accumulation and foam cell formation, characteristics of the onset of atherogenesis. In certain embodiments, a compound of formula I or formula II competitively inhibits scavenger receptor-mediated LDL uptake. In certain embodiments, a compound of formula I or formula II competitively inhibits scavenger receptor-mediated LDL uptake in macrophages. In certain embodiments the scavenger receptor is SR-A. In certain embodiments the LDL is oxLDL.

Certain embodiments of the invention provide a method for preventing the uptake of LDL by a cell (e.g., a macrophage or a smooth muscle cell), comprising contacting the cell with a compound of formula I or formula II as described herein.

In certain embodiments, the cell expresses a scavenger receptor (e.g., SR-A or CD36).

In certain embodiments, a compound of formula I or formula II interacts with the scavenger receptor. In certain embodiments, a compound of formula I or formula II binds to the scavenger receptor.

By "inhibition of atherosclerotic development" is meant the suppression of the development, progression and/or severity of atherosclerosis, a slowly progressive disease characterized by the accumulation of cholesterol within the arterial wall, e.g. by inhibiting, preventing or causing the regression of an atherosclerotic plaque.

Accordingly, the invention also provides a method for inhibiting atherosclerosis or atherosclerotic development in a mammal (e.g., a human), comprising administering an anti-atherosclerosis or anti-atherosclerotic development amount of a compound of formula I or formula II as described herein, or a pharmaceutically acceptable salt thereof, to the mammal.

When a plurality of compounds of formula I or formula II are placed in a hydrophilic solvent (e.g., an aqueous solution comprising water or wherein the solvent is water) the compounds of formula I or formula II can aggregate, with the polyether portion of the compounds extending into the hydrophilic solvent, and the hydrophobic chain portions of the compounds forming a hydrophobic core. Such aggregates can solubilize a hydrophobic molecule (e.g., a hydrophobic therapeutic agent) in the aqueous solvent, by encapsulating the hydrophobic molecule in the hydrophobic core of the aggregates. The hydrophobic molecule can typically be added to the solution of the compounds of formula I or formula II subsequent to aggregation, or the hydrophobic molecule can be added to the solution of the compounds of formula I or formula II prior to aggregation, allowing the aggregates to form around the molecule. Thus, the aggregates formed from the compounds of formula I or formula II can function similar to traditional micelles.

Typically, the aggregates of the invention have a diameter of from about 10 nm to about 1000 nm. The diameters can be measured using any suitable analytical technique, such as, for example, dynamic light scattering.

Compounds of formula I and formula II can be used to form aggregates that function similar to conventional "micelles". These aggregates can be used for essentially any application in which conventional micelles are employed. Examples include drug solubilization, fragrance encapsulation, passive targeting for drug delivery, waste water treatment, enhanced capillary electrophoresis activation, and induction of protein crystallization.

Accordingly, as used herein, the term "molecule" includes any compound that can be incorporated into an aggregate as described herein. Typically, "molecules" have solubility properties that are undesirable and that can be modified by incorporation into an aggregate of the invention. For example, the term "molecule" includes therapeutic agents, insecticides, pesticides, herbicides, antiseptics, food additives, fragrances, dyes, diagnostic aids, and the like. Other specific examples of molecules include, but are not limited to:

abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene;

baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butlated hydroxyanisole, butylated hydroxytoluene;

calcium iodostearate, calcium saccharate, calcium stearate, capobenic acid, captan, carbamazepine, carbocloral, carbophenothin, carboquone, carotene, carvacrol, cephaeline, cephalin, chaulmoogfic acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofazimine, clofibrate, cloflucarban, cionitrate, clopidol, clorindione, cloxazolam, coroxon, corticosterone, coumachlor, coumaphos, coumithoate cresyl acetate, crimidine, crifomate, cuprobam, cyamemazine, cyclandelate, cyclarbamate cymarin, cypennethril;

dapsone, defosfamide, deltamethrin, deoxycorticocosterone acetate, desoximetasone, 10 dextromoramide, diacetazoto, dialifor, diathymosulfone, decapthon, dichlofluani, dichlorophen, dichlorphenamide, dicofol, dicryl, dicmarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicofinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscomacetate, ethylhydrocupreine, ethyl menthane carboxamide, eugenol, euprocin, exalamide;

febarbamate, fenalamide, fenbendazole, fenipentol, fenitrothion, fenofibrate, fenquizone, fenthion, feprazone, fIilpin, filixic acid, floctafenine, fluanisone, flumequine, fluocortin butyl, fluoxymesterone, flurothyl, flutazolam, fumagillin, 5-furfuryl-5-isopropylbarbitufic acid, fusafungine, glafenine, glucagon, glutethimide, glybuthiazole, griseofulvin, guaiacol carbonate, guaiacol phosphate, halcinonide, hematoprphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione;

josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, nafialofos, nafiopidil, naphthalene, 2-naphthyl lactate, 2-(2-naphthyloxy)ethan01, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone;

octavefine, oleandrin, oleic acid, oxazepam, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl-6-chlorophenol, phentlmethylbarbituric acid, phenytoin, phosalone, phthalylsulfathiazole, phylloquinone, picadex, pifamine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate;

quercetin, quinbolone, quizalofo-ethyl, rafoxanide, rescinnamine, rociverine, ronnel salen, scarlet red, siccmn, simazine, simetfide, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiace a zone, thiocolchicine, thiocftc acid, thioquinox, thioridazine, thiram, thymyl N-isoamylcarbamate, tioxidazole, tioxolone, tocopherol, tolciclate, tolnafiate, triclosan, triflusal, triparanol;

ursolic acid, valinomycin, verapamil, vinblastine, vitamin A, vitamin D, vitamin E, xenbucin, xylazine, zaltoprofen, and zearalenone.

The aggregates of the invention are particularly useful for solubilizing hydrophobic molecules, particularly therapeutic agents that are hydrophobic in nature. Thus, according to one embodiment of the present invention, a therapeutic agent is encapsulated by combining the agent and a plurality of compounds of formula I or formula II in a solvent, such as water. The present invention contemplates the use of encapsulated hydrophobic molecules at concentrations ranging from $10^{-3}$ to $10^{-6}$ M. At the same time, another advantage of the present invention is the thermodynamic stability of the polymers, which permit the formation of low concentration stable aqueous solutions of the polymer encapsulates, far below the CMC's of conventional surfactants. CMC values range from $10^{-4}$ to $10^{-7}$ M but may be as low as $10^{-10}$ which is below the limits of detection. CMC is the critical micellar concentration, the concentration at which a majority of the polymers are comprised within micellar aggregates vs. individual polymer chains.

The compounds and aggregates of the can also be used for delivering a variety of nucleic acids. In some embodiments the nucleic acid is a therapeutic agent. Accordingly, in one embodiment the invention provides a composition comprising a compound of formula I or formula II or a salt thereof and a nucleic acid (e.g. DNA, RNA or siRNA). In another embodiment, the invention provides a pharmaceutical composition comprising a compound of formula I or formula II or a pharmaceutically acceptable salt thereof and a nucleic acid (e.g. DNA, RNA or siRNA) and a pharmaceutically acceptable carrier. In another embodiment, the invention provides a composition comprising a compound of formula I or formula II or a salt thereof and a lipid and a nucleic acid (e.g. DNA, RNA or siRNA). In another embodiment, the invention provides a pharmaceutical composition comprising a compound of formula I or formula II or a pharmaceutically acceptable salt thereof and a lipid and a nucleic acid (e.g. DNA, RNA or siRNA) and a pharmaceutically acceptable carrier. In another embodiment, the invention provides a method for delivering a nucleic acid (e.g. DNA, RNA or siRNA) into a cell comprising contacting the cell with a composition comprising a compound of formula I or formula II or a salt thereof and the nucleic acid under conditions such that the nucleic acid is delivered into the cell. In another embodiment, the invention provides a method for delivering a nucleic acid (e.g. DNA, RNA or siRNA) into a cell comprising contacting the cell with a composition comprising compound of formula I or formula II or a salt thereof and a lipid and the nucleic acid under conditions such that the nucleic acid is delivered into the cell.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably. Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The present invention further provides a method of substantially silencing a target gene of interest or targeted allele for the gene of interest in order to provide a biological or therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect. As used herein, the term "biological effect" refers to a change in the behavior of a cell, tissue or organism. Biological effects encompass a wide range of behaviors that include but are not limited to changes in gene expression, metabolism, growth, motility, or response to environmental perturbations. Biological effects can be measured by a qualified scientist or technician using assays specific to the biological effect under study.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest. As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

The encapsulates of the invention that comprise a therapeutic agent can be formulated as pharmaceutical compositions and administered to a mammalian host, such as a human patient in a variety of forms adapted to the chosen route of administration, i.e. parenterally, by intravenous, intramuscular, topical or subcutaneous routes. Thus, the encapsulates of the invention may be systemically administered, in combination with a pharmaceutically acceptable vehicle such as an inert diluent.

The encapsulates of the invention may be administered intravenously or intraperitoneally by infusion or injection. Solutions of the encapsulates can be prepared, for example, in water. Under ordinary conditions of storage and use, these preparations may contain a preservative to prevent the growth of microorganisms.

The pharmaceutical dosage forms suitable for injection or infusion should be sterile, fluid and stable under the conditions of manufacture and storage. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the encapsulates of the invention in the required amount in the appropriate solvent with various of the other ingredients enumerated above, as required, followed by sterilization.

The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved.

A typical dosage might range from about 0.001 mg to about 1,000 mg of therapeutic agent, per kg of animal weight. Preferred dosages range from about 0.01 mg/kg to about 100 mg/kg, and more preferably from about 0.10 mg/kg to about 20 mg/kg. Advantageously, the dosage forms of this invention may be administered several times daily, and other dosage regimens may also be useful.

According to the invention, aggregate degradation is not a prerequisite for release of the molecule (e.g. the therapeutic agent).

The compounds of formula I and formula II and aggregates thereof may also be used as thickening agents, lubricants, detergents surfactants, plasticizers and anti-fouling agents. The compounds of formula I or formula II, aggregates and encapsulates of the invention may be used as an emulsifying, dispersing or stabilizing agent for dyes, cosmetics, pigment and pharmaceutical products. The compounds of formula I or formula II, aggregates and encapsulates of the invention are particularly useful as an, emulsifying, dispersing or stabilizing agent in the dyeing of textiles and for encapsulating dyes, fragrances, or both for cosmetics. The compounds of formula I or formula II, aggregates and encapsulates of the invention are useful as lubricants and as a thickening agents for paints. The compounds of formula I or formula II, aggregates and encapsulates of the invention may also be employed as an emulsifying, dispersing or stabilizing agent for components of photographic compositions and developers.

For therapeutic applications, the preferred aggregates of the invention hydrolyze into components known to be biocompatible, i.e., sugars, fatty acids, amino acids and poly(ethylene glycol). This also results in low cytotoxicity of the polymer and its hydrolysis products. The poly(alkylene oxide) units enhance the immunogenicity of the encapsulate, enabling the hydrophobic molecules to evade the body's immune system, thereby increasing the circulation time of the hydrophobic molecule. This allows for effective treatment with reduced quantities of the hydrophobic molecule, which, together with the enhanced immunogenicity, prevents or reduces the severity of incidents of toxic side effect.

The following non-limiting examples set forth herein below illustrate certain aspects of the invention.

As described herein, amphiphilic macromolecules (AMs) based on carbohydrate domains functionalized with poly (ethylene glycol) can inhibit the uptake of oxidized low density lipoprotein (oxLDL) and counteract foam cell formation, a key characteristic of early atherogenesis. To investigate the influence of lipophilicity and stereochemistry on the AMs' physicochemical and biological properties, mucic acid-based AMs bearing four aliphatic chains (2a) and tartaric acid-based AMs bearing two (2b and 2l) and four aliphatic chains (2g and 2k) were synthesized and evaluated. Solution aggregation studies suggested that both the number of hydrophobic arms and the length of the hydrophobic domain impact AM micelle sizes, whereas stereochemistry impacts micelle stability. 2l, the meso analogue of 2b, elicited the highest reported oxLDL uptake inhibition values (89%), highlighting the crucial effect of stereochemistry on biological properties. This study suggests that stereochemistry plays a critical role in modulating oxLDL uptake and must be considered when designing biomaterials for potential cardiovascular therapies.

Nanoscale amphiphilic macromolecules (AMs) capable of inhibiting oxLDL uptake through competitive inhibition of SR-A and CD36 scavenger receptors in IC21 macrophage cells have been reported (Chnari, E.; et al., Biomacromolecules 2006, 7, 1796-1805). Comprised of a mucic acid backbone, four aliphatic chains, and a poly(ethylene glycol) (PEG) tail, these biocompatible AMs (2a) (FIG. 1A), form nanoscale micelles in aqueous media at relatively low critical micelle concentrations ($10^{-7}$ M) (Tian, L.; Yam, L.; Zhou, N.; Tat, H.; Uhrich, K. E. Macromolecules 2004, 370, 538-543). To determine the key structural components critical for oxLDL uptake inhibition, this AM structure has been systematically varied to determine the role of PEG chain length and architecture, carboxylic acid location, type and number of anionic charges, and rotational motion of the anionic group (Iverson, N. M.; Sparks, S. M.; Demirdirek, B.; Uhrich, K. E.; Moghe, P. V. Acta Biomaterialia 2010, 6, 3081-3091). The role that comparative hydrophobicity and stereochemistry play in inhibiting oxLDL uptake, however, has not been actively explored. Based on previous molecular modeling and experimental studies, the hydrophobic domain of these AMs appears to be actively involved in binding to macrophage scavenger receptors ((a) York, A. W.; Zablocki, K. R.; Lewis, D. R.; Gu, L.; Uhrich, K. E.; Prud'homme, R. K.; Moghe, P. V. Adv Mater 2012, 24, 733-739; (b) Hehir, S.; Plourde, N. M.; Gu, L.; Poree, D. E.; Welsh, W. J.; Moghe, P. V.; Uhrich, K. E. Acta Biomater 2012, 8, 3956-3962; (c) Plourde, N. M.; Kortagere, S.; Welsh, W.; Moghe, P. V. Biomacromolecules 2009, 10, 1381-1391; (d) Chnari, E.; Nikitczuk, J. S.; Wang, J.; Uhrich, K. E.; Moghe, P. V. Biomacromolecules 2006, 7, 1796-1805). These previous studies correlate well with literature that suggests that hydrophobic interactions play a major role in protein-polymer complexation (Petit, F.; Audebert, R.; Iliopoulos, I. Colloid Polym Sci 1995, 273, 777-781; Porcar, I.; Cottet, H.; Gareil, P.; Tribet, C. Macromolecules 1999, 32, 3922-3929; Gao, J. Y.; Dubin, P. L., Binding of Proteins to Copolymers of varying Hydrophobicity. Biopolymers 1999, 49, 185-193).

The effect of lipophilicity on the polymer's physicochemical and biological properties, has been investigated by comparing (2a) to an analogous AM comprised of an L-tartaric acid (L-TA) backbone bearing only two aliphatic chains (2b) (FIG. 1a). Investigating the physicochemical properties of these two AMs showed that an increase in lipophilicity rendered more stable micelles, as determined by the critical micelle concentration (CMC, a measure of solution stability), with larger hydrodynamic radii. To investigate the impact of lipophilicity on their biological properties, these AMs were tested for their ability to inhibit oxLDL uptake in peripheral blood mononuclear cells (PBMCs) under serum-free conditions. While both polymers inhibited oxLDL uptake, (2a) was more efficacious, inhibiting 52% of oxLDL uptake in PBMCs compared to 35% inhibition achieved by (2b) (FIG. 1B). Although these results may suggest that lipophilicity impacts physicochemical and biological properties, it should be noted that the sugar backbones of (2a) and (2b) have different stereochemistries; mucic acid is a chiral, optically inactive, meso compound and L-TA is chiral, but optically active. Studies have demonstrated that stereochemistry can greatly impact a polymer's physicochemical and biological properties (Hehir, S.; Plourde, N. M.; Gu, L.; Poree, D. E.; Welsh, W. J.; Moghe, P. V.; Uhrich, K. E. Acta Biomater 2012, 8, 3956-3962; Reeve, M. S.; Mccarthy, S. P.; Downey, M. J.; Gross, R. A. Macromolecules 1994, 27, 825-831; Sun, T.; Han, D.; Riehemann, K.; Chi, L.; Fuchs, H. S J Am Chem Soc 2007, 129, 1496-1497; Wang, X.; Gan, H.; Sun, T. L.; Su, B. L.; Fuchs, H.; Vestweber, D.; Butz, S. Soft Matter 2010, 6, 3851-3855; Wang, X. G., H.; Sun, T. Adv Func Mater 2011, 21, 3276-3281). Furthermore, because chirality influences numerous biological events/processes, stereoselective interactions between chiral materials and biological systems has been the topic of recent reviews (Sun, et al., Chem. Soc. Rev. 2011, 40, 2909-2921; Zhang, et al., Chem. Soc. Rev. 2012, 41, 1972-1984). It is, therefore, possible that this disparity in the properties of (2a) and (2b) is a consequence of lipophilicity, stereochemistry, or both.

Described herein is the synthesis of novel nanoscale AMs comprised of an L-TA backbone that bears four aliphatic chains, which were evaluated to ascertain the influence of lipophilicity on polymer properties. Preparation of these AMs was achieved in two manners: (1) growing dendrons from the hydroxyl groups of L-TA, thus incorporating branching onto the sugar backbone (i.e., dendronized) or (2) coupling two L-TA backbones to each other, yielding an AM with a disugar backbone (i.e., disugar). The physicochemical properties of these polymers was assessed as well as their ability to inhibit oxLDL uptake in PBMC macrophages. Additionally, a meso analog of (2b) was prepared (called (2l)) to determine the influence of stereochemistry on the AM properties.

Synthetic Materials

All reagents and solvents were purchased from Sigma-Aldrich and used as received unless otherwise noted. HPLC grade solvents were used unless otherwise noted. 4-(dimethylamino)pyridinium p-toluene-sulfonate (DPTS) was prepared as described by Moore and Stupp (Moore, J. S.; Stupp, S. I., Room-Temperature Polyesterification. Macromolecules 1990, 23 (1), 65-70). Monomethoxy-poly(ethylene glycol) (mPEG, Mn=5000 Da) was azeotropically distilled with toluene prior to use. The following compounds were prepared as previously described: (2a) (Tian, L.; et al., Amphiphilic scorpion-like macromolecules: Design, synthesis, and characterization. Macromolecules 2004, 37 (2), 538-543), (2b) (Tao, L.; Uhrich, K. E., Novel amphiphilic macromolecules and their in vitro characterization as stabilized micellar dug delivery systems. J Colloid Interface Sci 2006, 298 (1), 102-110), and benzylidene protected 2,2-bis (hydroxymethyl)propionic acid (BP-BMPA) (Ihre, H.; et al., Fast and Convenient Divergent Synthesis of Aliphatic Ester Dendrimers by Anhydride Coupling. J Am Chem Soc 2001, 123, 5908-5917). (2l), a structural analogue of (2b), was also prepared using the same procedure as (2b), but using meso-tartaric acid monohydrate. Prior to use, meso-tartaric acid monohydrate was azeotropically distilled with toluene to remove water (3×50 mL) and dried under high vacuum for 4 hours.

Instrumentation $^1$H-NMR spectra were obtained using a Varian 400 MHz or 500 MHz spectrophotometer with TMS as internal reference. Samples were dissolved in $CDCl_3$, or $CDCl_3$ with a few drops of DMSO-$d_6$ if necessary. IR spectra were recorded on a ThermoScientific Nicolet is 10 series spectrophotometer using OMNIC software by solvent-casting samples on a salt plate. Mass spectrometry was done on ThermoQuest Finnigan LCQ-DUO system that includes a syringe pump, an optional divert/inject valve, an atmospheric pressure ionization (API) source, a mass spectrometer (MS) detector, and the Xcalibur data system. Samples were prepared at a concentration of 10 µg/mL in HPLC-grade $CH_2Cl_2$. Molecular weights (MW) were determined using size exclusion chromatography (SEC) with respect to PEG standards (Sigma-Aldrich) on a Waters Stryagel® HR 3 THF column (7.8×300 mm). The Waters LC system (Milford, Mass.) was equipped with a 2414 refractive index detector, a 1515 isocratic HPLC pump, and 717 plus autosampler. Samples (10 mg/mL) were dissolved in THF and filtered using 0.45 pun pore size nylon or PTFE syringe filters (Fisher Scientific). Dynamic light scattering (DLS) analysis was carried out on a Zetasizer nanoseries ZS90 (Malvern instruments) in triplicate. Critical micelle concentration (CMC) studies were carried out on a Spex fluoromax-3 spectrofluorometer (Jobin Yvon Horiba) at 25° C. in triplicate.

Compounds of formula I can be prepared as illustrated in Scheme 1 and described in the examples. Compounds of formula I with different hydrophobic chains or different fatty acid residues, polyether moieties, number of hydroxy groups or different X, Y, Z, $X^1$, T, W or $W^1$ values can also be prepared by these same general procedures.

Scheme 1: Synthesis of linear disugar AM (2g)

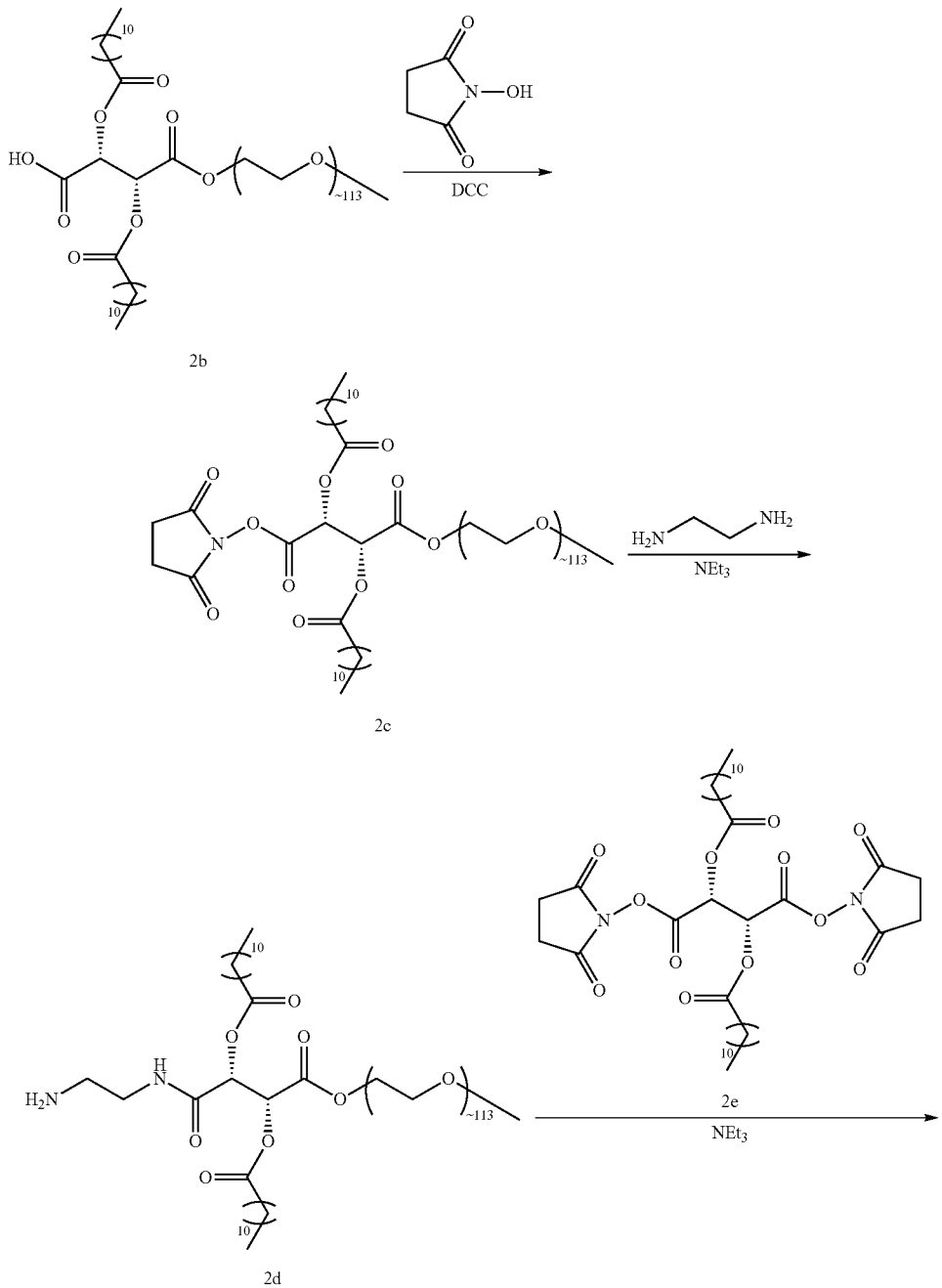

-continued

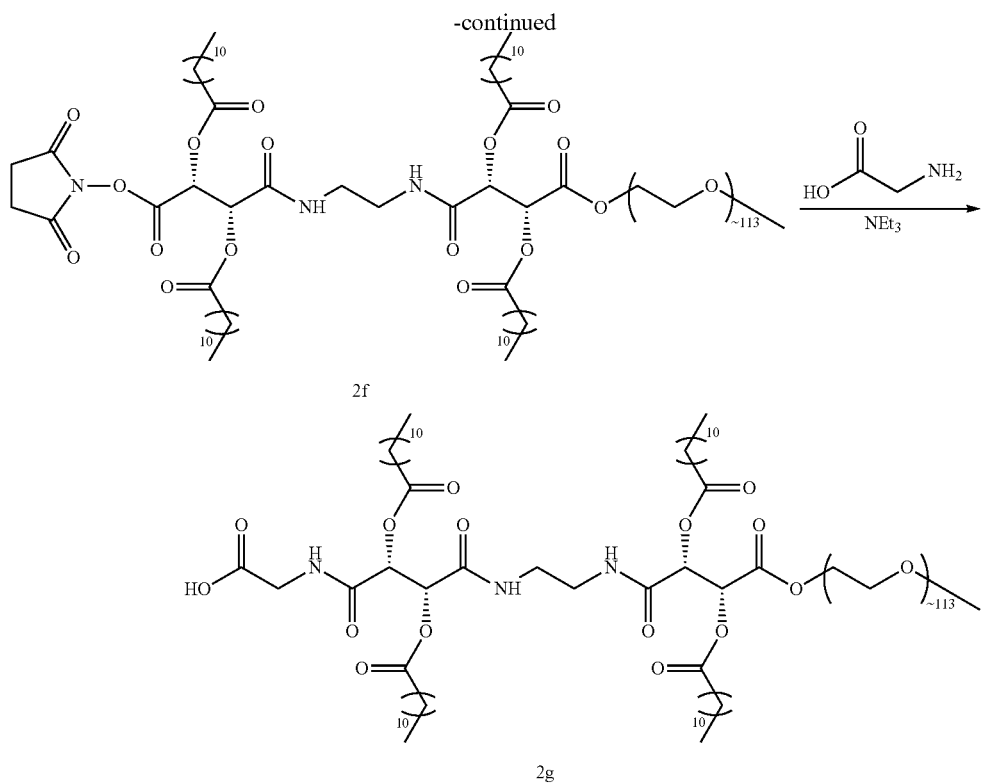

2f

2g

Preparation of novel nanoscale AMs based on L-tartaric acid (L-TA) and bearing 4 aliphatic chains was achieved via two synthetic methods: (1) coupling two L-TA backbones, yielding an AM with a linear backbone (referred to as "linear disugar" herein); and (2) incorporating branch points by growing dendrons from the L-TA hydroxyl groups (referred to as "dendronized"). The linear disugar AM was prepared by esterification of the previously synthesized (2b) (Tao, L.; Uhrich, K. E. *J Colloid Interface Sci* 2006, 298, 102-110) with N-hydroxysuccinimide (NHS) to yield (2c). The NHS group was subsequently displaced by ethylene diamine to form the amine-terminated AM, (2d). Coupling of this polymer to a di-NHS, lauryl-acylated L-tartaric acid (2e) yielded the NHS-capped linear disugar, (2f). Amidation using glycine rendered the carboxylic acid-terminated disugar, (2g), as the final product (Scheme 1). Polymers prepared at each step in the synthesis were characterized via $^1$H NMR and SEC.

Example 1

Preparation of Compound 2g

Preparation of Compound 2c

Compound (2c) was prepared in the same manner as the previously synthesized 0 cM (Djordjevic, J.; et al., Amphiphilic Scorpion-like Macromolecules as Micellar Nanocarriers. *J Bioact Compat Pol* 2008, 23 (6), 532-551), using (2b) (1.06 g, 0.19 mmol), N-hydroxysuccinimide (NHS) (0.09 g, 0.77 mmol), and N'-dicyclohexylcarbodiimide (DCC) (1 M in DCM) (0.31 mL) to yield (2c) as a white powder (0.92 g, 85%). $^1$H NMR (CDCl$_3$): δ=0.86 (t, 6), 1.26 (m, 32), 1.60 (b, 4), 2.39 (b, 4), 2.90 (s, 4), 3.41 (m, ~400), 5.66 (s, 2); M$_W$=5.5 kDa; PDI=1.07.

Preparation of Compound 2d

Compound (2d) was prepared similar to the previously prepared 1N (Sparks, S. M.; et al., Efficient Intracellular siRNA Delivery by Ethyleneimine-Modified Amphiphilic Macromolecules. *Macromolecular Bioscience* 2011, 11, 1192-1200), using (2c) (0.51 g, 0.09 mmol), propylamine (48.7 μL, 0.73 mmol), and triethylamine (NEt$_3$) (197.4 μt, 1.42 mmol) to yield (2d) as a white powder (0.42 g, 82%). $^1$H NMR (CDCl$_3$): δ=0.85 (t, 6), 1.21 (m, 32), 1.58 (b, 4), 2.28 (b, 4), 3.38 (s, 2), 3.41 (m, ~400), 4.42 (s, 2), 5.30 (s, 1), 5.74 (s, 1); M$_W$=5.6 kDa; PDI=1.06.

Preparation of Compound 2e

Lauryl-acylated tartaric acid (Tao, L.; Uhrich, K. E., Novel amphiphilic macromolecules and their in vitro characterization as stabilized micellar drug delivery systems. *J Colloid Interface Sci* 2006, 298 (1), 102-110) (0.30 g, 0.59 mmol) and NHS (0.27 g, 2.36 mmol) were weighed into a round bottom flask and placed under Ar(g). Anhydrous dichloromethane (DCM) and 6 mL anhydrous dimethyl formamide (DMF) were then added to the round bottom flask to dissolve the reagents. 1.48 mL DCC (1 M in DCM) was added dropwise to the reaction flask over one hour via syringe pump. The reaction mixture was stirred at room temperature under argon for 24 hours, cooled and the resulting white solid precipitate (dicyclohexylurea) was removed by vacuum filtration. The filtrate was washed with 0.1 N HCl (20 ml), followed by 50:50 brine:water (2×20 mL), dried over MgSO$_4$ and concentrated via rotary evaporation. The product was precipitated from hexanes yielding (2e) as a white solid (0.42 g, 29%). IR (cm-1, thin film from CHCl$_3$): 1831, 1745. $^1$H NMR (CDCl$_3$): δ=0.87 (t, 6), 1.26 (m, 32), 1.65 (m, 4), 2.48 (t, 4), 2.83 (s, 8), 6.23 (s, 2). $^{13}$C NMR (CDCl$_3$): 14.34, 22.91, 24.58, 25.73, 29.46, 29.57, 29.68, 29.85, 32.14, 33.50, 68.61, 161.75, 167.98, 172.18. [M+NH$_4$]$^+_{theo}$=726.9, GC-MS: [M+NH$_4$]$^+_{calc}$=726.1.

Preparation of Compound 2f

Compound (2d) (0.12 g, 0.02 mmol) was added to a round bottom flask and dissolved in 5 mL anhydrous DCM and 5 mL anhydrous DMF. After the addition of NEt$_3$ (50 µL, 0.36 mmol), the reaction mixture was allowed to stir under Ar(g). (2e) (0.015 g, 0.02 mmol) was dissolved in DCM (5 mL) and added dropwise to the reaction flask via syringe pump at a rate of 1 mL/hr. Upon complete (2e) addition, the reaction was allowed to stir at room temperature under argon for 24 hours. The reaction was filtered to remove insoluble triethylamine salts. The filtrate was washed with 0.1 N HCl (20 ml), followed by 50:50 brine:water (2×20 ml), dried over MgSO$_4$ and concentrated via rotary evaporation. The product was precipitated from diethyl ether yielding (2f) as a white solid (0.097 g, 75%). $^1$H NMR (CDCl$_3$): δ=0.85 (t, 6), 1.21 (m, 32), 1.58 (b, 4), 2.28 (b, 4), 3.38 (s, 2), 3.41 (m, ~400), 4.42 (s, 2), 5.30 (s, 1), 5.74 (s, 1); M$_W$=5.6 kDa; PDI=1.06.

Preparation of Compound 2g

Glycine (0.0015 g, 0.02 mmol) was added to a round bottom flask and dissolved in anhydrous DCM (5 mL) and anhydrous DMF (5 mL). Upon addition of NEt$_3$ (10 µL, 0.07 mmol), the reaction mixture was allowed to stir under Ar(g). (2f) (0.03 g, 0.005 mmol) was dissolved in 5 mL DCM and added dropwise to the reaction flask via syringe pump at a rate of 1 mL/hr. Upon complete (2e) addition, the reaction was allowed to stir at room temperature under argon for 24 hours. The reaction was filtered to remove insoluble triethylamine salts. The filtrate was washed with 0.1 N HCl (20 ml), followed by 50:50 brine:water (2×20 ml), dried over MgSO$_4$ and concentrated via rotary evaporation. The product was precipitated from diethyl ether yielding (20 as a white solid (0.01 g, 33%). $^1$H NMR (CDCl$_3$): δ=0.87 (t, 12), 1.21 (m, 64), 1.59 (b, 8), 2.38 (b, 8), 3.41 (m, ~400), 5.50 (s, 2); M$_W$=6.3 kDa; PDI=1.07.

Compounds of formula II can be prepared as illustrated in Scheme 2 and described in the examples. Compounds of formula II with different hydrophobic chains or different fatty acid residues, polyether moieties, number of hydroxy groups or different R$^3$, W or W$^1$ values can also be prepared by these same general procedures.

Scheme 2: Synthesis of dendritic (branched) nanoscale AM (2k)

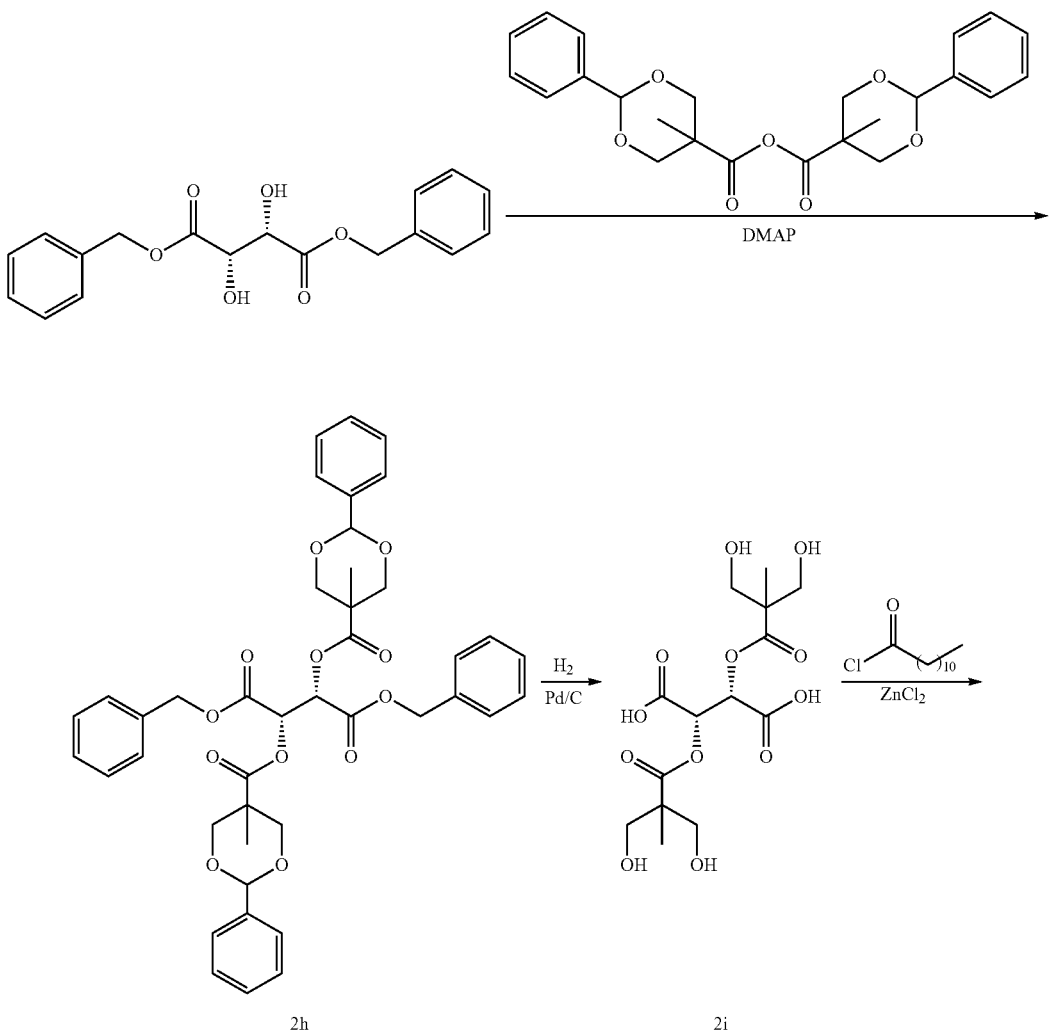

-continued

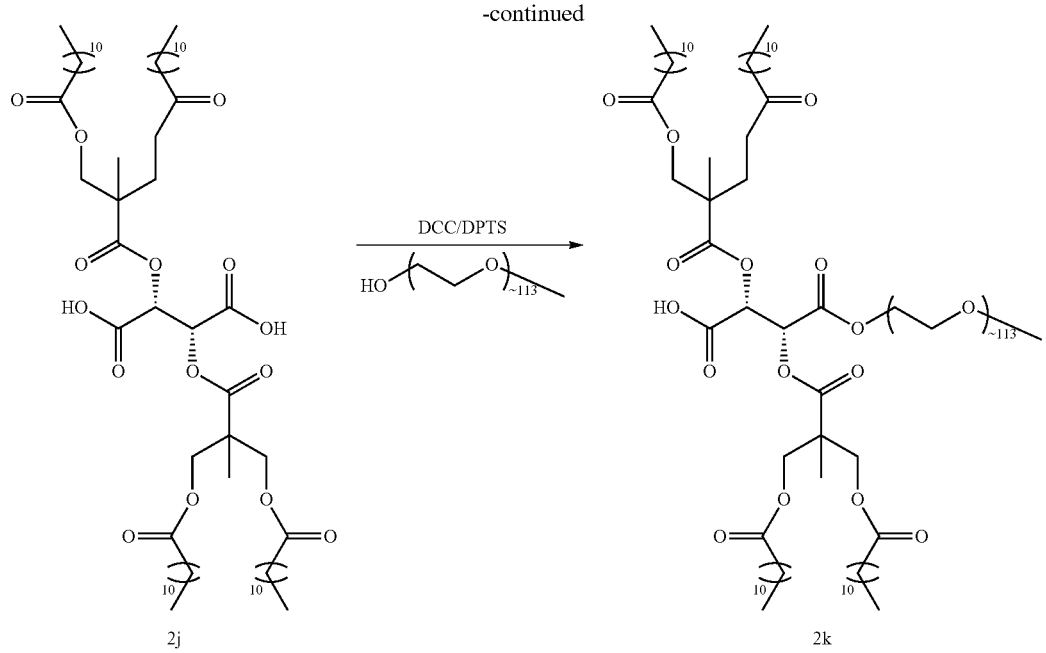

The synthesis of the dendronized AM was based on a divergent synthesis using an anhydride coupling developed by Ihre et al (Fast and Convenient Divergent Synthesis of Aliphatic Ester Dendrimers by Anhydride Coupling. *J Am Chem Soc* 2001, 123, 5907-5917). (Scheme 2). Dibenzyl-L-tartrate was coupled with the previously reported benzylidene-protected 2,2,-bis(hydoxymethyl) propionic acid (BP-BMPA) anhydride using N,N'-dimethylaminopyridine (DMAP) as the acylating catalyst to afford (2h) at a 92% yield. The benzylidene protecting groups as well as the benzyl esters were removed by catalytic hydrogenolysis using $H_2(g)$ and 10% w/w Pd/C as catalyst. Upon removal of catalyst by filtration, the deprotection rendered L-TA with four terminal hydroxyl groups (2i) in near quantitative yields. Using the dendronized L-TA, the corresponding AM was synthesized by modifying a previously published method for the preparation of (2a), which has a mucic acid backbone (Tian, L.; et al., Amphiphilic scorpion-like macromolecules: Design, synthesis, and characterization. *Macromolecules* 2004, 37 (2), 538-543). Briefly, the two-step procedure involves acylating (2i) with lauroyl groups followed by coupling to PEG (Scheme 2). During the initial acylation step, some modifications were required when (2i) was used in place of mucic acid. For example, to achieve an acceptable yield (40%) of (2j), the number of equivalents of acylating agent (lauroyl chloride) was significantly reduced from 15 (with mucic acid) to 5 (with dendronized L-TA), as isolation and purification proved problematic with a large excess of lauroyl chloride. It was also necessary that the reaction occur at room temperature and in solvent (DCM). Coupling of the PEG and (2j) using DCC as the coupling agent and DPTS as the catalyst proceeded as reported, yielding the dendritic AM, (2k), in 85% yield. The resultant polymer was characterized via SEC and $^1H$ NMR.

Example 2

Preparation of Compound 2K

Preparation of Compound 2h

Compound (2h) was prepared using an established literature procedure (Ihre, H.; et al., Fast and Convenient Divergent Synthesis of Aliphatic Ester Dendrimers by Anhydride Coupling. *J Am Chem Soc* 2001, 123, 5907-5917) using dibenzyl-L-tartrate (0.33 g, 0.99 mmol), BP-BMPA anhydride (1.05 g, 2.46 mmol) and 4-dimethylaminopyridine (DMAP) (0.06 g, 0.49 mmol), yielding (2h) as light yellow crystals (0.67 g, 92%). IR (cm-1, thin film from $CHCl_2$): 3458, 3328, 1736. $^1H$ NMR ($CDCl_3$): δ=1.01 (s, 6), 3.59 (dd, 4), 4.58 (dd, 4), 4.72 (d, 2), 5.02 (d, 2), 5.44 (s, 2), 5.84 (s, 2), 7.25 (m, 20). $^{13}C$ NMR ($CDCl_3$): 17.76, 42.91, 68.21, 71.42, 73.22, 73.73, 101.99, 126.54, 128.25, 128.30, 128.66, 134.85, 138.04, 165.45, 172.62.

Preparation of Compound 2i

Compound (2i) was prepared using an established literature procedure, (Ihre, H.; et al., Fast and Convenient Divergent Synthesis of Aliphatic Ester Dendrimers by Anhydride Coupling. *J Am Chem Soc* 2001, 123, 5907-5917) using (2h) (0.65 g) 10% w/w Pd/C, HPLC grade DCM (15 mL), and HPLC grade methanol (15 mL), yielding (2i) as white crystals (0.31 g, 97%). IR (cm-1, thin film from THF): 3408 (br), 1742. $^1H$ NMR ($CDCl_3$): δ=1.01 (s, 6), 3.52 (m, 8), 5.39 (s, 2). $^{13}C$ NMR ($CDCl_3$): 17.76, 42.91, 68.21, 71.42, 73.22, 73.73, 165.45, 172.62.

Preparation of Compound 2j

Compound (2i) (0.36 g, 0.95 mmol), lauroyl chloride (1.1 mL, 4.76 mmol), and zinc chloride (0.04 g, 0.30 mmol) were added to a round bottom flask. Anhydrous DCM (2 mL) was added and the reaction was stirred at room temperature under argon for 24 hours. Water (5 mL) and diethyl ether (10 mL) were added to quench the reaction. After stirring for one hour, the reaction mixture was diluted with diethyl ether (20 mL) and washed with water (5×20 mL), dried over $MgSO_4$ and concentrated via rotary evaporation. The product was precipitated from cold hexanes (refrigerated for 2 days) yielding (2j) as a white crystals (0.34 g, 32%). IR (cm-1, thin film from $CH_2Cl_2$): 3514, 1746. $^1H$ NMR ($CDCl_3$): δ=0.86 (t, 12), 1.26 (m, 70), 1.59 (b, 8), 2.29 (t, 8), 4.16 (m, 8), 5.62 (s, 2). $^{13}C$ NMR ($CDC_{13}$): 13.08, 17.79, 21.67, 23.58, 23.68, 27.90, 28.05, 28.13, 28.16, 28.23, 28.32, 28.36, 28.38, 28.43, 28.55, 28.57, 30.89, 32.12, 32.31, 42.91, 68.21, 71.42, 73.22, 73.73, 165.45, 168.12. $[M-2H]^-_{theo}$=1109.1, GC-MS: $[M-2H]^-$=1109.2.

Preparation of Compound 2k

Compound (2k) was prepared using an established literature procedure, (Tian, L.; et al., Amphiphilic scorpion-like macromolecules: Design, synthesis, and characterization. *Macromolecules* 2004, 37 (2), 538-543), using (2j) (0.20 g, 1.8 mmol), mPEG (0.28 g, 0.06 mmol), DCC (0.19 mL, 1.9 mmol), and 4-(dimethylamino)pyridinium p-toluene-sulfonate (DPTS) (0.02 g, 0.007 mmol) to yield (2k) as a white powder (0.29 g, 85%). $^1H$ NMR ($CDCl_3$): δ=0.88 (t, 12), 1.30 (m, 70), 1.61 (b, 8), 2.29 (t, 8), 3.63 (m, ~400H), 4.18 (m, 8), 5.5 (s, 1), 5.7 (s, 1); $M_W$=6.3 kDa; PDI=1.15.

Example 3

Critical Micelle Concentration (CMC) Measurements and C Log P Calculations

Materials and Methods

A solution of pyrene, a fluorescence probe molecule, was made up to a concentration of $5×10^{-6}$ M in acetone. Samples were prepared by adding 1 mL of pyrene solution to a series of vials and allowing the acetone to evaporate. AMs were dissolved in HPLC grade water and diluted to a series of concentrations from $1×10^{-3}$M to $1×10^{40}$ M. AM-pyrene solutions (10 mL) were shaken overnight at 37° C. to allow partition of the pyrene into the micelles. The concentration of pyrene in all samples was $5×10^{-7}$ M. Emission was performed from 300 to 360 nm, with 390 nm as the excitation wavelength. The maximum absorption of pyrene shifted from 332 to 334.5 nm on micelle formation (Astafieva, I. et al., Critical Micellization Phenomena in Block Polyelectrolyte Solutions. *Macromolecules* 1993, 26 (26), 7339-7352; Meng, F. B. et al., Mesomorphic Behavior and Optical Properties of Liquid-Crystalline Polysiloxanes Bearing Different Chiral Groups. *J Appl Polym Sci* 2009, 114 (4), 2195-2203; Kalyanasundaram, K. and Thomas, J. K., Environmental effects on vibronic band intensities in pyrene monomer fluorescence and their application in studies of micellar systems. *J Am Chem Soc* 1977, 99 (7), 2039-2044). The ratio of absorption of encapsulated pyrene (334.5 nm) to pyrene in water (332 nm) was plotted as the logarithm of polymer concentrations. The inflection point of the curve was taken as the CMC.

C log P values were derived using the CambridgeSoft ChemDraw software. The calculated values were of the AM hydrophobic domain as the PEG component was constant for all polymers.

Results

With these unique AMs, the impact of hydrophobicity on the physicochemical properties, namely hydrodynamic radius and critical micelle concentration (CMC), was evaluated (Table 1). CMC values were measured using a previously reported fluorimetry technique using pyrene as the fluorescence probe (Astafieva, et al., *Macromolecules* 1993, 26, 7339-7352). The linear disugar AM, (2g), formed micelles of ~117 nm in diameter while the dendronized AM, (2k), formed ~17 nm micelles (Table 1). The larger micelles formed by (2g) may be attributed to the increased length of the hydrophobic core, a consequence of tethering two L-TA sugars. A similar trend was observed by Zeng and Pitt (*J. Biomater Sci., Polym. Ed.* 2006, 17, 591-604) who, when preparing the amphiphilic copolymer poly(ethylene oxide)-b-poly(N-isopropylacrylamide(NIPAAM)-co-2-hydroxyl-ethyl methacrylate-lactate$_n$), observed that lengthening of the hydrophobic poly(NIPAAM) block resulted in larger micelles. Both AMs exhibited C log P values (2g: 17.36, 2k: 21.00) similar to that of their 4-arm, mucic acid-based analogue, (2a) (20.37) (Table 1). These results suggest that micelle size is influenced by the number of hydrophobic arms as well as by the length of the hydrophobic domain, i.e., overall lipophilicity. In regards to micelle assembly, both (2g) and (2k) have CMC values on the order of $10^{-5}$M, similar to that of (2b) (Table 1). Each of these polymers possess an L-TA backbone which suggests that the stereochemistry of the hydrophobic core plays a key role in micelle self-assembly.

Table 1 below lists hydrodynamic size, CMCs measurements and the hydrophobicity coefficient (C log P).

TABLE 1

Physicochemical properties of AMs
The hydrodynamic size and critical micelle concentrations were experimentally measured; The hydrophobicity coefficient was estimated for the non-PEG components of AMs.

| Polymer | Size (nm)$^a$ | CMC (M) | ClogP |
|---|---|---|---|
| (2a) | 20 | 1.20 * 10−7 | 20.37 |
| (2b) | 7 | 1.25 * 10−5 | 9.09 |
| (2g) | 117 | 1.58 * 10−5 | 17.38 |
| (2k) | 17 | 5.84 * 10−5 | 21.00 |
| (2l) | 8 | 6.12 * 10−6 | 9.09 |

$^a$Z-average

Example 4

LDL Oxidation

Oxidized low density lipoprotein (oxLDL) was generated by incubating 50 μg/ml LDL purified from human plasma (Molecular Probes Eugene, Oreg.) with 10 μM $CuSO_4$ at 37° C. for 18 hr exposed to air (Chang, M. Y.; et al., Oxidized LDL bind to nonproteoglycan components of smooth muscle extracellular matrices. *J Lipid Res* 2001, 42 (5), 824-833, Oorni, K.; et al., Oxidation of low density lipoprotein particles decreases their ability to bind to human aortic proteoglycans—Dependence on oxidative modification of the lysine residues. *J Biol Chem* 1997, 272 (34), 21303-21311). Oxidation was terminated with 0.01% w/v EDTA (Sigma, St. Louis, Mo.).

Example 5

OxLDL Accumulation in PBMCs

Material and Methods
Cell Culture and oxLDL Oxidation

Peripheral blood mononuclear cells (PBMCs) were isolated from human buffy coats (Blood Center of New Jersey; East Orange, N.J.) by centrifugation through Ficoll-Paque density gradient (GE Healthcare). PBMCs were plated into T-175 flasks, and monocytes were selected via plastic adherence by washing thrice with phosphate buffered saline (PBS) after 24 hours. Monocytes were cultured for 7 days in RPMI 1640 (ATCC) supplemented with 10% fetal bovine serum (FBS), 1% Penicillin/Streptomycin, and 50 ng/mL M-CSF (macrophage colony-stimulating factor) for differentiation into macrophages.

PBMC-derived macrophages were co-cultured with 10 μg/mL of 3,3'-dioctadecyloxacarbocyanine (DiO) labeled oxLDL (Kalen Biomedical) and NLB micelles ($10^{-5}$ to $10^{-7}$ M) for 24 hours in serum-free RPMI 1640. Cells were then fixed with 4% paraformaldehyde and counterstained with Hoechst 33342 prior to epifluorescent imaging using a Nikon Eclipse TE2000-S. Oxidized LDL uptake was quantified using ImageJ and normalized to conditions receiving no polymer treatment.

Statistical Analysis

Each in vitro experiment was performed at least twice and three replicate samples were investigated in each experiment. Five images per well were captured and analyzed. The results were then evaluated using analysis of variance (ANOVA). Significance criteria assumed a 95% confidence level ($P<0.05$). Standard error of the mean is reported in the form of error bars on the graphs of the final data.

Results

Figure 2:
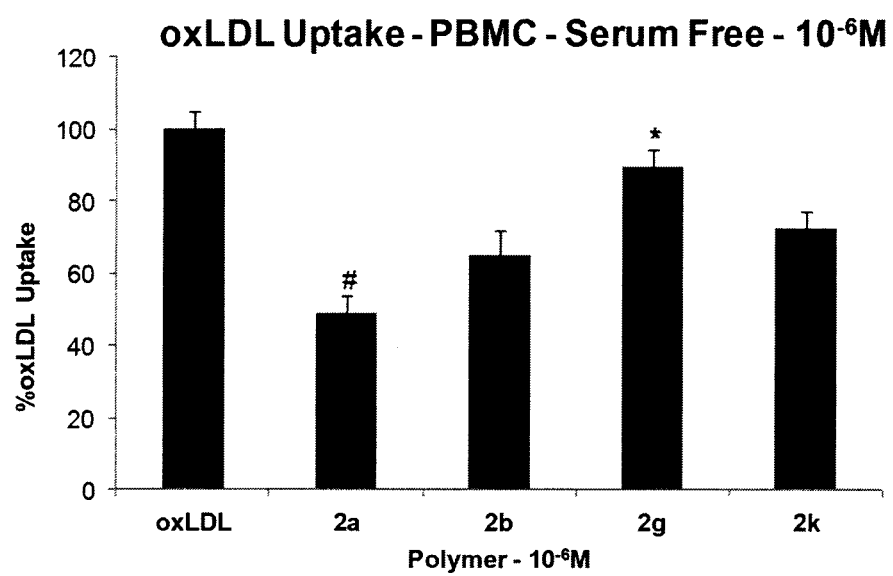
FIG. 2 shows the evaluation and role of AMs with varying hydrophobicity on the in vitro inhibition of oxLDL uptake in PBMC macrophages.

As shown in FIG. 2, the new AMs were assessed for their ability to inhibit oxLDL internalization in peripheral blood mononuclear cell (PBMC) macrophages. These in vitro experiments were carried out by incubating the cells with $10^{-6}$ M polymers and fluorescently labeled oxLDL for 24 hours at 37° C. As a control, the basal uptake of oxLDL when no polymer was present was evaluated. The previously synthesized (2a) (Tian et al., *Macromolecules* 2004, 37, 538-543) and (2b) (Tao, L.; Uhrich, K. E. *J Colloid Interface Sci* 2006, 298, 102-110) were compared to the newly synthesized polymers (FIG. 2). Based on the improved inhibition of oxLDL internalization of (2a) (52%) relative to (2b) (35%) (FIG. 2), it was anticipated that increasing the overall hydrophobicity of the L-TA based polymers would result in decreased oxLDL internalization. The converse, however, was observed; both (2g) and (2k) were far less efficacious in inhibiting oxLDL uptake (11% and 27% inhibition, respectively) (FIG. 2). This result suggests that just the extrinsic hydrophobicity of AMs does not uniquely govern blockage of macrophage oxLDL uptake mechanisms but that other factors likely contribute to (2a)'s improved efficacy of oxLDL inhibition.

Example 6

Influence of Stereochemistry on AM Physicochemical and Biological Properties—AM (2l)

Because (2a) and (2b) differ not only in their overall lipophilicity, but also in stereochemistry, the influence of stereochemistry on AM physicochemical and biological properties was probed. A new AM (2l) (FIG. 3*a*) was prepared to be structurally analogous to (2b) while being stereochemically analogous to (2a). Specifically, (2l), a structural analogue of (2b), was prepared using the same procedure as (2b) (see Synthetic Materials section above), but using meso-tartaric acid monohydrate. Prior to use, meso-tartaric acid monohydrate was azeotropically distilled with toluene to remove water (3×50 mL) and dried under high vacuum for 4 hours.

Figure 3:
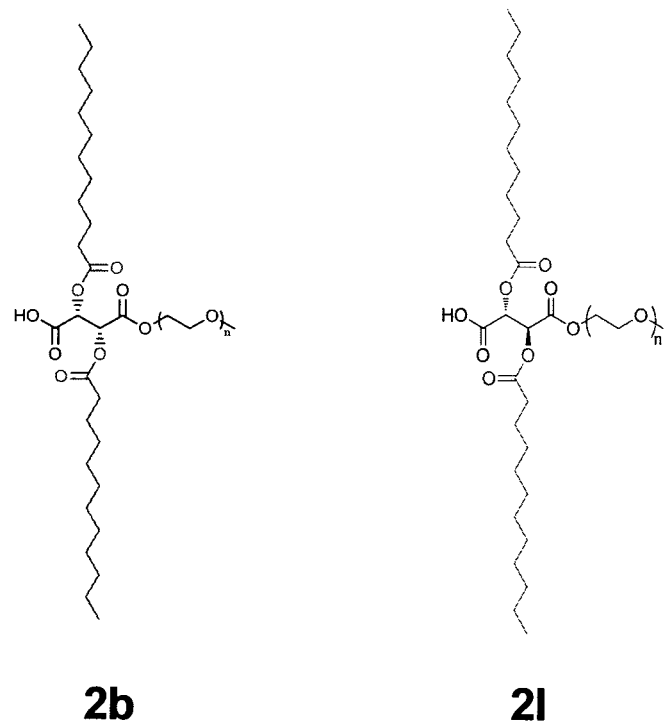
FIG. 3A shows the chemical structure of AM bearing 2-aliphatic arms (2b) and an equivalent AM with meso stereochemistry (2l).
FIG. 3B shows the effect of stereochemistry on the in vitro inhibition of oxLDL uptake in PBMC macrophages.
Figure 3:
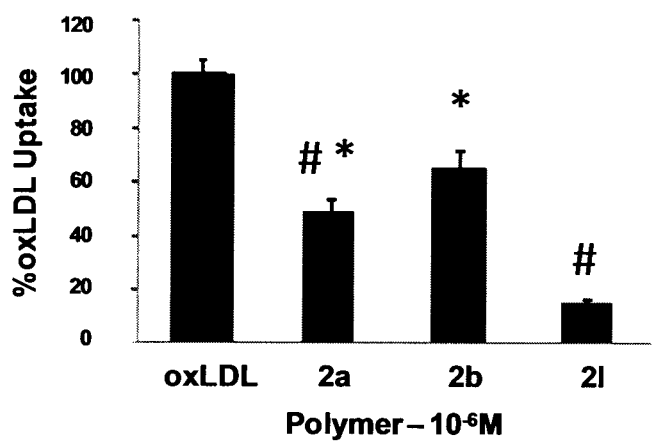

Analysis of the solution behavior of (2l) revealed micelles that were similar in size (~8 nm) to (2b), but more stable (CMC values of $10^{-6}$ M as opposed to $10^{-5}$ M) under physiological conditions (Table 1, Example 3). These findings correlate well with the results described in the above Examples—the number of hydrophobic arms and the length of the hydrophobic domain influence micelle size while stereochemistry influences the solution stability of micelles. The (2l) AM was also assessed for its ability to inhibit oxLDL internalization in peripheral blood mononuclear cell (PBMC) macrophages, as described in Example 5. The results show that minute changes, such as altering one stereocenter along the polymer's sugar backbone, greatly affects oxLDL uptake and also revealed (2l) as a better inhibitor to oxLDL uptake than the "gold standard", (2a) (FIG. 3*b*). Although it has less overall lipophilicity relative to (2a), (2l) showed the highest degree of inhibition of oxLDL internalization, 89% (FIG. 3*b*). This result further demonstrates that overall AM lipophilicity may not be the most critical factor in governing oxLDL inhibition, but rather, stereochemistry of the hydrophobic domain could dramatically influence the polymer-blockage of oxLDL uptake.

As described above, the inventors have discovered that the amphiphilic molecule (2l) is useful in inhibiting the uptake of LDL and thus may be useful for treating athereosclerosis.

Accordingly, the invention also provides a compound of formula (2l):

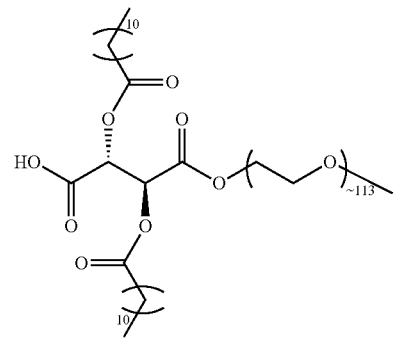

or a salt thereof.

In another embodiment the invention provides a compound of formula III:

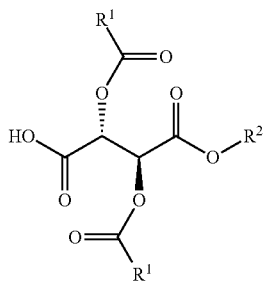

III wherein: each R¹ is independently a hydrophobic chain; and each R² is a polyether; or a salt thereof. The terms "hydrophobic chain" and "polyether" are used as defined herein. It is to be understood that any of the values for R¹ and R² described herein can be used for the compound of formula III.

When a bond in a compound described herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound of formula III or formula (21) is at least 51% the absolute stereoisomer depicted. In another embodiment, the compound of formula III or formula (21) is at least 60% the absolute stereoisomer depicted. In another embodiment, the compound of formula III or formula (21) is at least 80% the absolute stereoisomer depicted. In another embodiment, the compound of formula III or formula (21) is at least 90% the absolute stereoisomer depicted. In another embodiment, the compound of formula III or formula (21) is at least 95 the absolute stereoisomer depicted. In another embodiment, the compound of formula III or formula (21) is at least 99% the absolute stereoisomer depicted.

The invention also provides a pharmaceutical composition comprising a compound of formula III or formula (21) or a pharmaceutically acceptable salt thereof, and a pharmaceutically acceptable carrier.

The invention also provides a method for reducing LDL in a mammal (e.g., a human) comprising administering an effective amount of a compound of formula III or formula (21), or a pharmaceutically acceptable salt thereof, to the mammal.

The invention also provides a method for preventing the uptake of LDL by a cell comprising contacting the cell with a compound of formula III or formula (21).

The invention also provides a method for inhibiting atherosclerosis or atherosclerotic development in a mammal (e.g., a human), comprising administering an anti-atherosclerosis or anti-atherosclerotic development amount of a compound of formula III or formula (21), or a pharmaceutically acceptable salt thereof, to the mammal.

The invention also provides a compound of formula III or formula (21) or a pharmaceutically acceptable salt thereof for use in medical therapy.

The invention also provides a compound of formula III or formula (21) or a pharmaceutically acceptable salt thereof for the prophylactic or therapeutic treatment of atherosclerosis.

The invention also provides the use of a compound of formula III or formula (21) or a pharmaceutically acceptable salt thereof to prepare a medicament for inhibiting atherosclerosis or atherosclerotic development in a mammal (e.g., a human).

The invention also provides the use of a compound of formula III or formula (21) or a pharmaceutically acceptable salt thereof to prepare a medicament for reducing LDL in a mammal (e.g., a human).

The invention also provides the use of a compound of formula III or formula (21) or a pharmaceutically acceptable salt thereof to prepare a medicament for preventing the uptake of LDL by a cell in a mammal (e.g., a human).

The invention also provides intermediates and processes useful for preparing compounds of formula III or the compound of formula (21) as described herein.

In cases where compounds are sufficiently basic or acidic, a salt of a compound of formula III or formula (21) can be useful as an intermediate for isolating or purifying a compound of formula III or formula (21). Additionally, administration of a compound of formula III or formula (21) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula III or formula (21) can be formulated as pharmaceutical compositions and administered to a mammalian host, such as a human patient in a variety of forms adapted to the chosen route of administration, i.e., orally or parenterally, by intravenous, intramuscular, topical or subcutaneous routes. Thus, the compositions of the invention may be systemically administered, in combination with a pharmaceutically acceptable vehicle such as an inert diluent.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Useful dosages of a compound of formula III or formula (21) can be determined by comparing their in vitro activity, and in vivo activity in animal models. Methods for the extrapolation of effective dosages in mice, and other animals, to humans are known to the art; for example, see U.S. Pat. No. 4,938,949. Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain embodiments of the invention provide a composition comprising a plurality of compounds of formula III or formula (21), as described herein, in a solvent, wherein the compounds of formula III or formula (21) form one or more aggregate structures.

In certain embodiments, the solvent comprises water.

In certain embodiments, the solvent is water.

As used herein, the term "aggregate" means a plurality of compounds of formula III or formula (21) in a solvent that have organized into an ordered structure, for example, a structure having a hydrophobic core and a surrounding hydrophilic layer, or a structure having a hydrophilic core and a surrounding hydrophobic layer.

As used herein, the term "a plurality of compounds of formula III or formula (21)" means more than one compound of formula III or formula (21). In such a plurality, each compound can have the same structure, or the plurality can include compounds that have differing structures. For example, in one embodiment, the term "a plurality of compounds of formula III" means more than one compound of formula III, wherein each of the compounds of formula III has the same structure.

In one embodiment the invention provides a composition comprising a plurality of compounds of formula III or formula (21) and one or more lipids.

As used herein, the term "encapsulate" means an aggregate, having a molecule (e.g., a therapeutic agent) surrounded or partially surrounded by a plurality of compounds of formula III or formula (21). In certain embodiments, the term "encapsulate" means an aggregate, having a molecule (e.g., a therapeutic agent) surrounded or partially surrounded by a plurality of compounds of formula III or formula (21) and one or more lipids.

As used herein, the term "stabilized encapsulate" means an aggregate, having a molecule (e.g., a therapeutic agent) surrounded or partially surrounded by a plurality of compounds of formula III or formula (21). In certain embodiments, the term "stabilized encapsulate" means an aggregate, having a molecule (e.g., a therapeutic agent) surrounded or partially surrounded by a plurality of compounds of formula III or formula (21) and one or more lipids.

As used herein, the phrase "low-density lipoprotein (LDL)" includes "unoxidized LDL," "weakly oxidized LDL" and "oxidized LDL." These terms are defined as described above.

By "reduction" or "reducing" is meant the separation or removal (e.g., lowered concentration of a substance, such as LDL) from a physiological sample or the blood stream of a subject. For example, in one embodiment of the invention, a compound of formula III or formula (21) is administered to a patient and becomes associated with LDL in a manner that will provide a beneficial physiological effect. For example, it is possible that the compound of formula III or formula (21) may cause certain forms of the LDL to be eliminated from a subject, or prevent other forms of LDL from having physiological and/or pathological activity. In certain embodiments, the compound of formula III or formula (21) may attach itself to LDL and cause the LDL to be eliminated from a subject, or prevent other forms of LDL from having physiological and/or pathological activity.

For example, it is also possible that the compound of formula III or formula (21) can inhibit the uptake of modified forms of LDL mediated by scavenger receptors (e.g., scavenger receptor A (SR-A) or CD36) and counteract cholesterol accumulation and foam cell formation, characteristics of the onset of atherogenesis. In certain embodiments, a compound of formula III or formula (21) competitively inhibits scavenger receptor-mediated LDL uptake. In certain embodiments, a compound of formula III or formula (21) competitively inhibits scavenger receptor-mediated LDL uptake in macrophages. In certain embodiments the scavenger receptor is SR-A. In certain embodiments the LDL is oxLDL.

Certain embodiments of the invention provide a method for preventing the uptake of LDL by a cell (e.g., macrophages or smooth muscle cells), comprising contacting the cell with a compound of formula III or formula (21) as described herein.

In certain embodiments, the cell expresses a scavenger receptor (e.g., SR-A or CD36).

In certain embodiments, a compound of formula III or formula (21) interacts with the scavenger receptor. In certain embodiments, a compound of formula III or formula (21) binds to the scavenger receptor.

The phrase "inhibition of atherosclerotic development" is defined as described herein.

When a plurality of compounds of formula III or formula (21) are placed in a hydrophilic solvent (e.g., an aqueous solution comprising water or wherein the solvent is water) the compounds of formula III or formula (21) can aggregate, with the polyether portion of the compounds extending into the hydrophilic solvent, and the hydrophobic chain portions of the compounds forming a hydrophobic core. Such aggregates can solubilize a hydrophobic molecule (e.g., a hydrophobic therapeutic agent) in the aqueous solvent, by encapsulating the hydrophobic molecule in the hydrophobic core of the aggregates. The hydrophobic molecule can typically be added to the solution of the compounds of formula III or formula (21) subsequent to aggregation, or the hydrophobic molecule can be added to the solution of the compounds of formula III or formula (21) prior to aggregation, allowing the aggregates to form around the molecule. Thus, the aggregates formed from the compounds of formula III or formula (21) can function similar to traditional micelles.

Typically, the aggregates of the invention have a diameter of from about 10 nm to about 1000 nm. The diameters can be measured using any suitable analytical technique, such as, for example, dynamic light scattering.

Compounds of formula III or formula (21) can be used to form aggregates that function similar to conventional "micelles". These aggregates can be used for essentially any application in which conventional micelles are employed. Examples include drug solubilization, fragrance encapsulation, passive targeting for drug delivery, waste water treatment, enhanced capillary electrophoresis activation, and induction of protein crystallization.

Accordingly, as used herein, the term "molecule" includes any compound that can be incorporated into an aggregate as described herein. Typically, "molecules" have solubility properties that are undesirable and that can be modified by incorporation into an aggregate of the invention. For example, the term "molecule" includes therapeutic agents, insecticides, pesticides, herbicides, antiseptics, food additives, fragrances, dyes, diagnostic aids, and the like. Other specific examples of molecules include, but are not limited to, those described above.

The aggregates of the invention are particularly useful for solubilizing hydrophobic molecules, particularly therapeutic agents that are hydrophobic in nature. Thus, according to one embodiment of the present invention, a therapeutic agent is encapsulated by combining the agent and a plurality of compounds of formula III or formula (21) in a solvent, such as water. The present invention contemplates the use of encapsulated hydrophobic molecules at concentrations ranging from $10^{-3}$ to $10^{-6}$ M. At the same time, another advantage of the present invention is the thermodynamic stability of the polymers, which permit the formation of low concentration stable aqueous solutions of the polymer encapsulates, far below the CMC's of conventional surfactants. CMC values range from $10^{-4}$ to $10^{-7}$ M but may be as low as $10^{-10}$ which is below the limits of detection. CMC is the critical micellar concentration, the concentration at which a majority of the polymers are comprised within micellar aggregates vs. individual polymer chains.

The compounds and aggregates of the invention can also be used for delivering a variety of nucleic acids. In some embodiments the nucleic acid is a therapeutic agent. Accordingly, in one embodiment the invention provides a composition comprising a compound of formula III or formula (21) or a salt thereof and a nucleic acid (e.g. DNA, RNA or siRNA). In another embodiment, the invention provides a pharmaceutical composition comprising a compound of formula III or formula (21) or a pharmaceutically acceptable salt thereof and a nucleic acid (e.g. DNA, RNA or siRNA) and a pharmaceutically acceptable carrier. In another embodiment, the invention provides a composition comprising a compound of formula III or formula (21) or a salt thereof and a lipid and a nucleic acid (e.g. DNA, RNA or siRNA). In another embodiment, the invention provides a pharmaceutical composition comprising a compound of formula III or formula (21) or a pharmaceutically acceptable salt thereof and a lipid and a nucleic acid (e.g. DNA, RNA or siRNA) and a pharmaceutically acceptable carrier. In another embodiment, the invention provides a method for delivering a nucleic acid (e.g. DNA, RNA or siRNA) into a cell comprising contacting the cell with a composition comprising a compound of formula III or formula (21) or a salt thereof and the nucleic acid under conditions such that the nucleic acid is delivered into the cell. In another embodiment, the invention provides a method for delivering a nucleic acid (e.g. DNA, RNA or siRNA) into a cell comprising contacting the cell with a composition comprising compound of formula III or formula (21) or a salt thereof and a lipid and the nucleic acid under conditions such that the nucleic acid is delivered into the cell.

The terms "nucleic acid" and "nucleotide sequence" are defined as described above. The terms "nucleic acid," "nucleic acid molecule," or "polynucleotide" are used interchangeably.

Certain embodiments of the invention encompass isolated or substantially purified nucleic acid compositions. The terms "isolated" or "purified" DNA molecule or RNA molecule are defined as described above. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The present invention further provides a method of substantially silencing a target gene of interest or targeted allele for the gene of interest in order to provide a biological or therapeutic effect. The terms "substantially silencing" or "substantially silenced" are defined as described above. The term "therapeutic effect" is defined as described above. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect. The term "biological effect" is defined as described above.

The terms "RNA interference," "RNAi", "small interfering RNA", "short interfering RNA", "siRNA", "short hairpin RNA", "shRNA" molecule, "miRNA", "RNA duplex" and "targeted" are defined as described above.

The encapsulates of the invention that comprise a therapeutic agent can be formulated as pharmaceutical compositions and administered to a mammalian host as described above.

According to the invention, aggregate degradation is not a prerequisite for release of the molecule (e.g. the therapeutic agent).

The compounds of formula III or formula (21) and aggregates thereof may also be used as thickening agents, lubricants, detergents surfactants, plasticizers and anti-fouling agents. The compounds of formula III or formula (21), aggregates and encapsulates of the invention may be used as an emulsifying, dispersing or stabilizing agent for dyes, cosmetics, pigment and pharmaceutical products. The compounds of formula III or formula (21), aggregates and encapsulates of the invention are particularly useful as an, emulsifying, dispersing or stabilizing agent in the dyeing of textiles and for encapsulating dyes, fragrances, or both for cosmetics. The compounds of formula III or formula (21), aggregates and encapsulates of the invention are useful as lubricants and as a thickening agents for paints. The compounds of formula III or formula (21), aggregates and encapsulates of the invention may also be employed as an emulsifying, dispersing or stabilizing agent for components of photographic compositions and developers.

For therapeutic applications, the preferred aggregates of the invention hydrolyze into components known to be biocompatible, i.e., sugars, fatty acids, amino acids and poly(ethylene glycol). This also results in low cytotoxicity of the polymer and its hydrolysis products. The poly(alkylene oxide) units enhance the immunogenicity of the encapsulate, enabling the hydrophobic molecules to evade the body's immune system, thereby increasing the circulation time of the hydrophobic molecule. This allows for effective treatment with reduced quantities of the hydrophobic molecule, which, together with the enhanced immunogenicity, prevents or reduces the severity of incidents of toxic side effect.

As described in the above Examples, innovative, nanoscale AMs were designed to investigate the influence of hydrophobicity and stereochemistry on physicochemical and biological properties. Solution aggregation studies indicate that micellar size is governed both by the number of hydrophobic arms and the length of the hydrophobic domain, whereas micelle stability is governed by the stereochemistry. In vitro experiments evaluating oxLDL inhibition displayed similar results: stereochemistry (not lipophilicity) of hydrophobic domain has a significant impact on oxLDL internalization. Thus for polymers with equivalent levels of hydrophobicity, the nature of the AM stereochemistry appears to be a critical parameter for modulating the anti-atherogenic activity of polymers. These insights could be relevant to the design of polymer therapeutics for the treatment of cardiovascular disease.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula II:

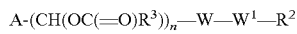

wherein;
A is selected from carboxy, —SO$_3$H and —PO$_3$H;
n is independently 2, 3, 4, 5 or 6;
W is —C(=O)—, —C(=S)—, or is absent;
W$^1$ is O, S or NH;
each R$^1$ is independently a hydrophobic chain;
R$^2$ is a polyether, wherein the polyether has the following structure:

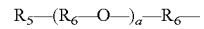

wherein R$_5$ is a 1 to 20 carbon straight-chain or branched alkyl group, —OH, —OR$_7$, —NH$_2$, —NHR$_7$, —NHR$_7$R$_8$, —CO$_2$H, —SO$_3$H (sulfo), —CH$_2$—OH, —CH$_2$—OR$_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;
R$_6$ is a 1 to 10 carbon straight-chain or branched divalent alkylene group;
each R$_7$ and R$_8$ is independently a 1 to 6 carbon straight-chain or branched alkylene group; and
a is an integer from 2 to 150, inclusive; and
each R$^3$ is independently (C$_1$-C$_8$)alkyl wherein each (C$_1$-C$_8$)alkyl is independently substituted with one or more —O(C=O)R$^1$ groups;
or a salt thereof.

2. The compound of claim 1 wherein the compound of formula II is a compound of formula IIa:

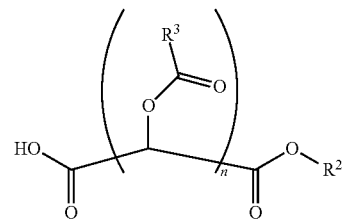

wherein:
n is 2, 3, 4, 5 or 6;
each R$^1$ is independently a hydrophobic chain;
R$^2$ is a polyether, wherein the polyether has the following structure:

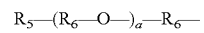

wherein R$_5$ is a 1 to 20 carbon straight-chain or branched alkyl group, —OH, —OR$_7$, —NH$_2$, —NHR$_7$, —NHR$_7$R$_8$, —CO$_2$H, —SO$_3$H (sulfo), —CH$_2$—OH, —CH$_2$—OR$_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;
R$_6$ is a 1 to 10 carbon straight-chain or branched divalent alkylene group;
each R$_7$ and R$_8$ is independently a 1 to 6 carbon straight-chain or branched alkylene group; and
a is an integer from 2 to 150, inclusive; and
each R$^3$ is independently (C$_1$-C$_8$)alkyl wherein each (C$_1$-C$_8$)alkyl is independently substituted with one or more —O(C=O)R' groups;
or a salt thereof.

3. The compound of claim 1 wherein the polyether is a poly(alkylene oxide) having between about 2 and about 150 repeating units.

4. The compound of claim 3, wherein each alkylene oxide unit comprises straight or branched ($C_2$-$C_4$) alkylene oxide.

5. The compound of claim 1 wherein the polyether is a poly(ethylene oxide) having between about 2 and about 150 repeating units.

6. The compound of claim 1, wherein the polyether comprises an alkoxy-terminal group.

7. The compound of claim 1 wherein the each $R^1$ is independently ($C_1$-$C_{24}$)alkyl, ($C_2$-$C_{24}$)alkene or ($C_2$-$C_{24}$) alkyne.

8. The compound of claim 1 wherein each $R^1$ is independently a fatty acid, wherein the fatty acid is caprylic, capric, lauric, myristic, myristoleic, palmitic, palmitoleic, stearic, oleic, linoleic, arachidic, behenic, or erucic acid, or a mixture thereof.

9. The compound of claim 1 wherein the each $R^1$ is independently a ($C_6$-$C_{18}$)alkyl.

10. The compound of claim 1 wherein n is independently 2 or 4.

11. The compound of claim 2 wherein each $R^3$ is independently a ($C_3$-$C_6$)alkyl.

12. The compound of claim 1 selected from:

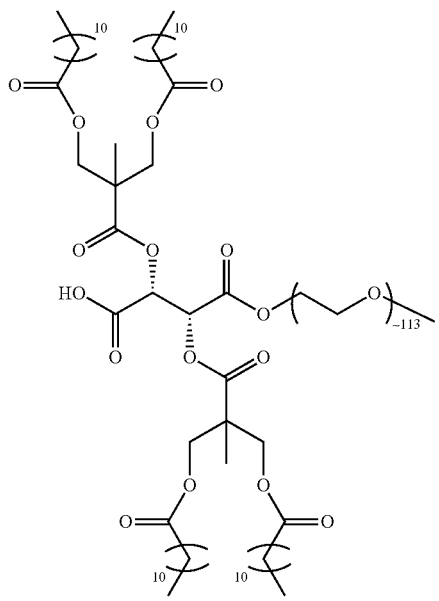

and

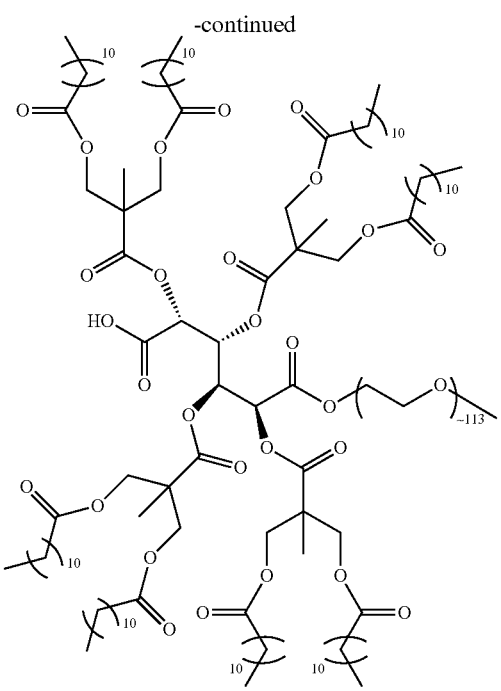

and salts thereof.

13. A pharmaceutical composition comprising a compound of formula II as described in claim 1, or a pharmaceutically acceptable salt thereof, and a pharmaceutically acceptable carrier.

14. A method for preventing the uptake of LDL by a cell comprising contacting the cell with a compound of formula II as described in claim 1.

15. A method for inhibiting atherosclerosis or atherosclerotic development in a mammal, comprising administering an anti-atherosclerosis or anti-atherosclerotic development amount of a compound of formula II as described in claim 1, or a pharmaceutically acceptable salt thereof, to the mammal.

16. The compound of claim 1, wherein A is carboxy.

17. The compound of claim 1, wherein W is —C(=O)—.

18. The compound of claim 1, wherein $W^1$ is O.

19. The compound of claim 1, wherein the polyether is a methoxy-terminated poly(ethylene oxide) having between about 2 and about 150 repeating units.

20. The compound of claim 1, wherein each $R^3$ is independently ($C_1$-$C_8$)alkyl wherein each ($C_1$-$C_8$)alkyl is independently substituted with two or more —O(C=O)$R^1$ groups.

* * * * *

UNITED STATES PATENT AND TRADEMARK OFFICE
CERTIFICATE OF CORRECTION

PATENT NO. : 9,434,681 B2  
APPLICATION NO. : 14/407403  
DATED : September 6, 2016  
INVENTOR(S) : Kathryn E. Uhrich, Dawanne E. Poree and Prabhas Moghe It is certified that error appears in the above-identified patent and that said Letters Patent is hereby corrected as shown below:

On the Title Page

Page 2, Item (56), Foreign Patent Documents, please delete "0105873 A1" and insert -- 01005873 A1 --;

Page 2, Item (56), Other Publications, please delete "Gammas, et al." and insert -- Cammas, et al. --;

Page 2, Item (56), Other Publications, Hehir, et al. citation, please delete "properties and bnding to" and insert -- properties and binding to --;

In the Claims

Column 42, Claim 2, Line 63, please delete "-O(C=O)R'" and insert the following:
-- -O(C=O)$R^1$ --

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*